United States Patent
Brown et al.

(10) Patent No.: US 8,404,722 B2
(45) Date of Patent: Mar. 26, 2013

(54) OXAZOLE COMPOUNDS COMPOSITIONS AND METHODS OF USE

(75) Inventors: Matthew Brown, San Francisco, CA (US); Michael G. Johnson, San Francisco, CA (US)

(73) Assignee: Amgen Inc., Thousand Oaks, CA (US)

( * ) Notice: Subject to any disclaimer, the term of this patent is extended or adjusted under 35 U.S.C. 154(b) by 169 days.

(21) Appl. No.: 12/920,258

(22) PCT Filed: Mar. 13, 2009

(86) PCT No.: PCT/US2009/001622
§ 371 (c)(1),
(2), (4) Date: Nov. 23, 2010

(87) PCT Pub. No.: WO2009/151495
PCT Pub. Date: Dec. 12, 2009

(65) Prior Publication Data
US 2011/0060011 A1    Mar. 10, 2011

Related U.S. Application Data

(60) Provisional application No. 61/070,005, filed on Mar. 18, 2008.

(51) Int. Cl.
A61K 31/4439    (2006.01)
A61K 31/42    (2006.01)
C07D 263/34    (2006.01)
C07D 413/04    (2006.01)

(52) U.S. Cl. ............... 514/340; 514/374; 546/271.4; 548/236

(58) Field of Classification Search ............... None
See application file for complete search history.

(56) References Cited

PUBLICATIONS

Lee et al., "A small-molecule antagonist of the hedgehog signaling pathway", Chembiochem, vol. 8, 2007.
Frank-Kamenetsky et al., "Small-molecule modulators of hedgehog signaling: identification and characterization of smoothened agonists and antagonists", Journal of Biology, vol. 1, No. 2, 2002.
Williams et al., "Identification of a small molecule inhibitor of the hedgehogsingaling pathway: effects on basal cell carcinoma-like lesions", Proc. Nat. Acad. Sci., vol. 100, No. 8, 2003.
Chen et al., "Small molecule modulation of smoothened activity", Proc. Nat. Acad. Sci., vol. 99, No. 22, 2002.
Berman et al., "Widespread requirement for hedgehog ligand stimulation in growth of digestive tract tumors", Nature, vol. 425, 846-851, 2003.
Berman et al., "Medulloblastoma growth inhibition by hedgehog pathway blockade", Science, vol. 297, 1559-1561, 2002.
Watkins et al., "Hedgehog signaling within airway epithelial progenitors and in small-cell lung cancer", vol. 422, 313-317, 2003.
Thayer et al., "Hedgehog is an early and late mediator of pancreatic cancer tumorignensis", Nature, 425: 851-856, 2003.
Borzillo et al., "The hedgehog signaling pathway as a target for anticancer drug discovery", Curr. Topics in Med. Chem, 5:147-157, 2005.

*Primary Examiner* — Kamal Saeed
(74) *Attorney, Agent, or Firm* — Joseph W. Bulock

(57) ABSTRACT

The present invention relates generally to compounds represented in Formula (I), pharmaceutical compositions comprising them and methods of treating of diseases or disorders such as cancer.

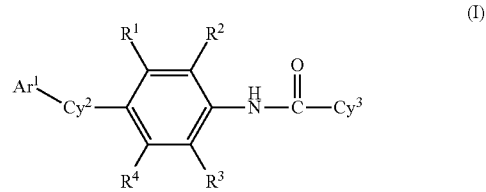

21 Claims, No Drawings

OXAZOLE COMPOUNDS COMPOSITIONS AND METHODS OF USE

FIELD OF THE INVENTION

This invention relates generally to the field of medicine and, more specifically, to oxazole compounds and pharmaceutical compositions comprising them, uses and methods for treating cancer.

BACKGROUND OF THE INVENTION

Members of the Hedgehog (Hh) family of signaling molecules mediate many important short and long range patterning processes during invertebrate and vertebrate development. Pattern formation is the activity by which embryonic cells form ordered spatial arrangements of differentiated issues. Hedgehog proteins were first discovered in *Drosophila*. Although some crucial differences exist, the signalling mechanisms are generally well conserved between *Drosophila* and higher organisms. In the fly, a single Hh gene regulates segmental and imaginal disc patterning. In contrast, in vertebrates, an Hh gene family is involved in the control of left-right asymmetry, polarity in the CNS, somites and limb, organogenesis, chondrogenesis and spermatogenesis. Three Hh homologues have been identified in humans: Sonic hedgehog (SHH), Indian hedgehog (IHH) and Desert hedgehog (DHH). The Hh signaling cascade is initiated by Hh binding to the Patched proteins (PTCH1 in humans) on the target cell. In the absence of the Hh ligand, PTCH1 represses the activity of Smoothened (SMO in humans, Smo in mouse and smo in *Drosophila*), a G-protein-coupled receptor (GPCR)-like protein. Mammalian Hh signaling requires the presence of nonmotile cilia to which SMO and other downstream pathway components localize to achieve activation of GLI transcription factors, the cubis interruptus (Ci) orthologues. The activator and repressor forms of Ci in mammals are represented by three separate zinc-finger proteins, with GLI1 and GLI2 functioning mostly as activators and GLI3 as a repressor. For review, see Rubin L. L. et al. (2006) *Nature Reviews*, vol 5, 1026-1033. The mechanism by which this signaling cascade regulates proliferation involves the activation of cyclins and cyclin-dependent kinases. The control of differentiation might be occurring via the production of other secreted proteins, including neurotrophic and angiogenic factors.

Medicinal chemistry efforts to identify inhibitors of Hh pathway began when Richard Keeler and co-workers isolated teratogens from *Veratrum califormicum* in 1964. Subsequent research established that the previously known alkaloid jervine and the newly discovered alkaloid cyclopamine were able to induce cyclopia. Almost four decades later, the heptahelical bundle of Smo was identified as the site of binding of cyclopamine using its photoaffinity and fluorescent derivatives. Chen, J. et al. (2002) *Genes & Develop.* 16: 2743-2748; Chen, J. et al. (2002) *Proc. Natl. Acad. Sci. USA* 99: 14071-14076; Frank-Kamenetsky, M. et al. (2002) *J. Biol.* 1, article 10. Several assays are used to screen for antagonists to Smo in vitro. One of the assays for high throughput screening examines the overall activity of the Hh pathway in a cellular context by determining the degree of activity of the downstream effector protein GLI. Chen et al., supra. Cell lines of this type often incorporate a GLI dependent luciferase reporter for the assay readout. The luciferase signal may be boosted by other engineer modifications, such as the addition of biologically active Shh, (e.g., Shh with an octyl moiety attached to its N terminus), or the utilization of cell lines that lack PTCH1 function. Alternatively, direct binding to Smo can be measured through the displacement of a fluorescent cyclopamine derivative. In addition, tumor xenograft models based on SCLC, biliary, prostate, pancreatic and medulloblastoma lines can also be used.

In the recent years it was established that aberrant activation of the Hh signaling pathway can lead to cancer. Gorlin syndrome (GS), or nevoid basal cell carcinoma syndrome, is an autosomal dominant genetic disease that is characterized by development abnormalities and tumor predisposition. Virtually all individuals with Gorlin syndrome develop basal cell carcinomas (BCC), usually at multiple sites, and are predisposed to other kinds of cancer as well, especially medulloblastoma, a tumor of cerebellar granule neuron progenitor cells, rhabdomyosarcoma, a muscle tumor, as well as ovarian fibromas and sarcomas. Borzillo, G. et al. (2005) *Curr. Topics in Med. Chem.* 5: 147-157.

BCC is the most common human cancer, accounting for about 70% of human skin cancers, and representing at least one third of all cancer diagnosed in the US each year. More than 99% of BCC cases arise sporadically in the population, with only 0.5% of cases arising in individuals with GS. BCC rarely metastasizes, but can be locally aggressive and recurrent. Inactivating mutations in PTCH1 occur most commonly in these tumors. A subset of BCC is driven via mutations in SMO, and these mutations activate the pathway by generating proteins with decreased sensitivity to PTCH1 suppression.

Medulloblastoma (MB) is a brain tumor that forms in the cerebellum of children and young adults, and may be the end result of defect in cerebellar organogenesis. MB, in addition to BCC, has a well recognized involvement of the Hh pathway. The outcome of this cancer is almost invariably poor. Surgery with subsequent radiation or chemotherapy increases survival to greater than 50%, but there is severe treatment-associated morbidity, including mental retardation. Hh-pathway antagonists have been tested in cell culture and mouse models of medulloblastoma. A new class of SMO-binding Hh antagonists has been demonstrated to be very potent. Berman C. M. et al. (2002) *Science* 297: 1559-1561.

Hh pathway has been implicated in many other types of cancer, including pancreatic cancer, other tumors of the gastrointestinal (GI) tract and prostate cancer. Abnormal expression of SHH, PTCH1 and SMO has been shown early in the formation of human pancreatic tumors. Thayer, S. P. et al. (2003) *Nature* 425: 313-317. Several pancreatic cancer cell lines were found to be PTCH1 and SMO-positive and growth inhibited in vitro by cyclopamine, suggesting an active autocrine loop through which tumor cells both make and respond to Hh ligand. Furthermore, systemic treatment with cyclopamine slowed the growth of tumors formed when these cell lines are implanted into immunocompromised mice. Similar observations were made for pancreatic and other GI tumors. Berman, D. M. et al. (2003) *Nature* 425: 846-851. Similar data was provided for prostate cancer as well, including SHH overexpression in tumor biopsies, especially in higher Gleason grade tumors, and in vitro and in vivo inhibitory effects of cyclopamine on growth of prostate cancer cell lines. The Hh pathway was further implicated in prostate tumor metastasis, as the capacity of AT6.3 cells to metastasize to the lung was completely abrogated by cyclopamine, and AT2.1, a rarely metastasizing clone, could be induced to metastasize by overexpression of GLI1, in a cyclopamine-insensitive manner.

It has been demonstrated recently that Hh may be involved in the development of a significant subset of small cell lung carcinoma (SCLC). Watkins, D. N. et al. (2003) *Nature* 422: 313-317. In this study, Shh pathway components were found to be reactivated in a mouse model of acute airway damage caused by naphthalene. About 50-70% of SCLC lines and primary tumors expressed transcripts (SHH, PTCH1, GLI1) indicative of activated Shh signaling. Cyclopamine blocked the growth of only those cells with persistent Hh signaling, and this effect was abrogated by overexpression of GLI1. None of the effects of cyclopamine could be reproduced with tomatidine, a compound that is structurally similar but inactive against SMO.

These results demonstrate that Hh pathway is an important pharmacological target for a variety of cancers. Compounds and compositions of the current invention present an important treatment option for all tumors driven by inappropriate Hh signaling.

SUMMARY OF THE INVENTION

The present invention relates to compounds of Formula I

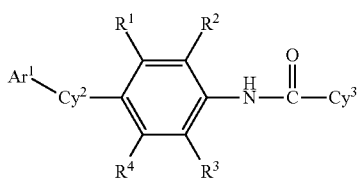

I or a pharmaceutically acceptable salt thereof, wherein all substituents are as defined in Detailed Description.

The invention provides pharmaceutical compositions comprising compounds of Formula I, solvates, prodrugs and or pharmaceutically acceptable salts thereof and a pharmaceutically acceptable carrier.

In one aspect, the invention provides methods of treating cancer, comprising administering a therapeutically effective amount of a compound of Formula I or a pharmaceutically acceptable salt thereof to a subject in need thereof. In one aspect, cancer can be pancreatic cancer. In another aspect, cancer can be basal cell carcinoma, medulloblastoma, Gorlin syndrome, prostate or lung cancer. The invention further provides methods for treating cancer, further comprising administering a compound selected from the group consisting of antibiotics, alkylating agents, antimetabolite agents, hormonal agents, immunological agents and interferon-type agents.

In one aspect, the invention provides methods of treating angiogenesis in a subject, comprising administering a therapeutically effective amount of a compound of Formula I or a pharmaceutically acceptable salt thereof to a subject in need thereof. In another aspect, the invention provides methods of reducing blood flow in a tumor in a subject, comprising administering a therapeutically effective amount of a compound of Formula I or a pharmaceutically acceptable salt thereof to a subject in need thereof.

In one aspect, the subject can be human.

DETAILED DESCRIPTION OF THE INVENTION

I. Definitions

"Treating" or "treatment" of a disease includes: inhibiting the disease, i.e., arresting or reducing the development of the disease or any of its clinical symptoms, preventing the disease, i.e., causing the clinical symptoms of the disease not to develop in a subject that may be or has been exposed to the disease or conditions that may cause the disease, or predisposed to the disease but does not yet experience or display symptoms of the disease, or relieving the disease, i.e., causing regression of the disease or any of its clinical symptoms.

The phrase "therapeutically effective amount" is the amount of the compound of the invention that will achieve the goal of prevention of the disorder or improvement in disorder severity and the frequency of incidence. The improvement in disorder severity includes the reversal of the disease, as well as slowing down the progression of the disease.

As used herein, "cancer" and "cancerous" refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon cancer, medulloblastoma, and head and neck cancer. While the term "cancer" as used herein is not limited to any one specific form of the disease, it is believed that the methods of the invention will be particularly effective for cancers which are found to be accompanied by aberrant signaling in Hh pathway.

Unless otherwise specified, the following definitions apply to terms found in the specification and claims:

The term "H" denotes a single hydrogen atom. This radical may be attached, for example, to an oxygen atom to form a hydroxyl radical.

The term "alkyl" by itself or as part of another substituent, means, unless otherwise stated, a straight or branched chain, or cyclic, saturated hydrocarbon having the indicated number of carbon atoms (i.e., $C_1$-$C_8$ means one to eight carbons). For example, $C_1$-$C_8$ alkyl is meant to include, but is not limited to methyl, ethyl, propyl, isopropyl, butyl, sec-butyl, tert-butyl, pentyl, isopentyl, neopentyl, hexyl, isohexyl, cyclohexyl, cyclohexylmethyl, cyclopropylmethyl and neohexyl.

The term "alkenyl" as used herein refers to a straight or branched chain unsaturated hydrocarbon having the indicated number of carbon atoms (i.e., $C_2$-$C_8$ means two to eight carbons) and at least one double bond. Examples of a $C_2$-$C_8$ alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene.

The term "alkylene" refers to a divalent alkyl group (e.g., an alkyl group attached to two other moieties, typically as a linking group). Examples of a ($C_1$-$C_8$) alkylene include —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, and —$CH_2CH_2CH_2CH_2CH_2CH_2CH_2$—, as well as branched versions thereof. The term "alkenylene" refers to a divalent alkenyl group (e.g., an alkenyl group attached to two other moieties, typically as a linking group). Examples of a $C_2$-$C_8$ alkenylene group include —CH═CH—, —$CH_2$CH═CH—, —$CH_2$CH═CH$CH_2$—, as well as branched versions thereof.

Typically, an alkyl, alkenyl, alkylene, or alkenylene group will have from 1 to 24 carbon atoms, with those groups having 10 or fewer carbon atoms being preferred in the present invention. A "lower alkyl" "lower alkenyl" or "lower alkylene" is a shorter chain alkyl or alkylene group, generally having eight or fewer carbon atoms.

The term "heteroatom" is meant to include oxygen (O), nitrogen (N), sulfur (S) and silicon (Si).

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heteroalkylene" and "heterocycloalkyl."

The term "cycloalkyl" by itself or in combination with other terms, represents, unless otherwise stated, cyclic version of "alkyl". Thus, the term "cycloalkyl" is meant to be included in the terms "alkyl". Examples of cycloalkyl include cyclopentyl, cyclohexyl, 1-cyclohexenyl, 3-cyclohexenyl, cycloheptyl, cyclobutylene, cyclohexylene and the like.

The term "aryl" as used herein refers to a 6- to 14-membered monocyclic, bicyclic or tricyclic aromatic hydrocarbon ring system. Examples of an aryl group include phenyl and naphthyl.

The term "heterocycle", "heterocyclic residue" or "heterocyclyl" as used herein refer to 3- to 14-membered ring systems which are either saturated, unsaturated, or aromatic, and which contain from 1 to 4 heteroatoms independently selected from nitrogen, oxygen and sulfur, and wherein the nitrogen and sulfur heteroatoms may be optionally oxidized, and the nitrogen heteroatom may be optionally quaternized, including monocyclic, bicyclic, and tricyclic ring systems. The bicyclic and tricyclic ring systems may encompass a heterocycle or heteroaryl fused to a benzene ring. The heterocycle may be attached via any heteroatom or carbon atom. Heterocycles include heteroaryls, heterocycloalkyls, and heterocycloalkenyls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl, and quinazolinyl. A heterocycle group can be unsubstituted or optionally substituted with one or more substituents as described herein below.

The term "alkoxy" as used herein refers to an —O-alkyl group. For example, an alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl. The term "alkoxyalkyl" refers to an alkoxy group appended to an alkyl radical. The term "aryloxy" as used herein refers to an —O-aryl group. The term "alkoxyaryl" refers to an alkoxy group attached to an aryl radical.

The term "amino" refers to a chemical functionality —NR'R", wherein R' and R' are independently hydrogen, alkyl or aryl.

The term "halo" or "halogen" as used herein refers to —F, —Cl, —Br or —I.

The term "haloalkyl," as used herein, refers to a $C_1$-$C_6$ alkyl group wherein one or more of the $C_1$-$C_6$ alkyl group's hydrogen atoms is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl. Thus, the term "haloalkyl" includes monohaloalkyl (alkyl substituted with one halogen atom) and polyhaloalkyl (alkyl substituted with halogen atoms in a number ranging from two to (2 m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example, the term "perhalo($C_1$-$C_4$)alkyl", is meant to include trifluoromethyl, pentachloroethyl, 1,1,1-trifluoro-2-bromo-2-chloroethyl, and the like.

The term "sulfonyl", whether used alone or linked to other terms such as alkylsulfonyl, denotes respectively divalent radicals —$SO_2$—.

The terms "carboxy" or "carboxyl", whether used alone or with other terms, such as "carboxyalkyl", denotes —$CO_2$H.

The term "carbonyl", whether used alone or with other terms, such as "aminocarbonyl", denotes —(C=O)—.

The term "aminocarbonyl" denotes an amide group of the formula —C(=O)$NH_2$.

The term "protected" with respect to hydroxyl groups, amine groups, carboxyl groups and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3$^{rd}$ Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

The compounds of the invention can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of the compounds of the invention, including tautomeric forms of the compound.

Certain compounds of the invention may have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, and mixtures thereof, including a racemic mixture. Optical isomers of the smoothened receptor modulators can be obtained by known techniques such as asymmetric synthesis, chiral chromatography, simulated moving bed technology or via chemical separation of stereoisomers through the employment of optically active resolving agents.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

A "pharmaceutically acceptable" denotes any salt or ester of a compound of this invention, or any other compound which upon administration to a patient is capable of providing (directly or indirectly) a compound of this invention, or a metabolite or residue thereof.

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al. (1977) J. Pharm. Sci. 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester, but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). Radiolabeled compounds are useful as therapeutic or prophylactic agents, e.g., cancer therapeutic agents, research reagents, e.g., assay reagents, and diagnostic agents, e.g., in vivo imaging agents. All isotopic variations of the compounds of the invention, whether radioactive or not, are intended to be encompassed within the scope of the invention.

It should be noted that if there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

II. Compounds that Modulate Smoothened Receptor and Pharmaceutical Compositions Comprising them, Administration and Dosage The present invention relates to compounds useful in treating cancer and angiogenesis as defined by Formula I

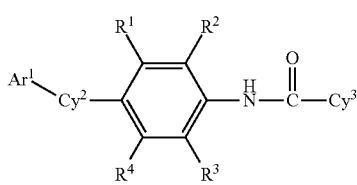

or a pharmaceutically acceptable salt thereof, wherein $Ar^1$ is phenyl or pyridinyl optionally substituted independently with 1-5 substituents, wherein the substituents are selected from the group consisting of $C_{1-8}$alkyl, $C_{1-8}$alkenyl, $C_{1-8}$alkynyl, $C_{1-6}$haloalkyl, halogen, cyano, hydroxy, oxo, —$NR^aR^b$ and —$OR^c$; $R^1$, $R^2$, $R^3$, and $R^4$ are each independently selected from H, $C_{1-6}$alkyl, $C_{1-6}$cycloalkyl, $C_{1-6}$haloalkyl, halogen, oxo, —C(=O)$OR^a$, —$R^c$OH, —$OR^c$, —$NR^aR^b$, $NR^aC$(=O)$R^b$, —C(=O)$OR^c$, —C(=O)$NR^aR^b$, —OC(=O)$R^c$, —$NR^aC$(=O)$R^c$, —$NR^aS$(=O)$_mR^c$, —S(=O)$_mNR^aR^b$, and S(=O)$_mR^c$; $R^a$, $R^b$, and $R^c$ are each independently selected from H, $C_{1-8}$alkyl, $C_{1-8}$alkenyl, $C_{1-8}$alkynyl, $C_{1-6}$haloalkyl, heterocyclyl, aryl, and heteroaryl; $Cy^2$ is selected from the group consisting of

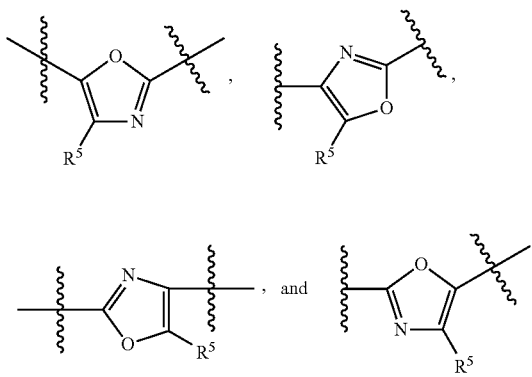

$R^5$ is H, $C_{1-6}$alkyl, $C_{1-6}$cycloalkyl, or $C_{1-6}$haloalkyl; $Cy^3$ is a partially or fully saturated or unsaturated 6-membered monocyclic ring formed of carbon atoms optionally including 1-3 heteroatoms selected from the group consisting of O, N, and S, wherein the ring is optionally substituted independently with 1-5 substituents, wherein the substituents are independently selected from the group consisting of $C_{1-8}$alkyl, $C_{1-8}$alkenyl, $C_{1-8}$alkynyl, $C_{1-6}$haloalkyl, halogen, cyano, hydroxy, oxo, —C(=O)$OR^c$, —$R^c$OH, —$OR^c$, —$NR^aR^b$, $NR^aC$(=O)$R^b$, —C(=O)$NR^aR^b$, —OC(=O)$R^c$, —$NR^aC$(=O)$R^c$, —$NR^aS$(=O)$_mR^c$, —S(=O)$_mNR^aR^b$, and S(=O)$_mR^c$, wherein the substituents can be fused forming a 5- or 6-membered saturated or unsaturated cycle optionally containing 1-3 heteroatomes selected from the group consisting of O, N, and S; provided that at least one of $Ar^1$ or $Cy^3$ is substituted with at least one substituent or $R^5$ is not H.

In one aspect, the invention encompasses compounds, or a pharmaceutically acceptable salt thereof, wherein $Ar^1$ is optionally substituted independently with 1-5 substituents, wherein the substituents are selected from the group consisting of $C_{1-8}$alkyl, $C_{1-8}$alkenyl, $C_{1-8}$alkynyl, $C_{1-6}$haloalkyl, halogen, cyano, hydroxy, oxo, —$NR^aR^b$ and —$OR^c$. In one aspect, $Ar^1$ can be unsubstituted pyridinyl. In another aspect, $Ar^1$ can be phenyl optionally substituted independently with 1-5 substituents, wherein the substituents are selected from the group consisting of $C_{1-8}$alkyl, $C_{1-8}$alkenyl, $C_{1-8}$alkynyl, $C_{1-6}$haloalkyl, halogen, cyano, hydroxy, oxo, —$NR^aR^b$ and —$OR^c$. In one aspect, phenyl can be substituted with 1 substituent selected from the group consisting of $C_{1-6}$haloalkyl and halogen. Halogen can be, for example, chlorine.

In one aspect, the invention provides compounds represented by Formula II

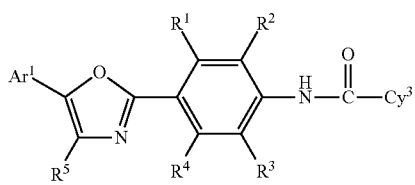

or a pharmaceutically acceptable salt thereof. In another aspect, the compounds of the invention can be represented by Formula III

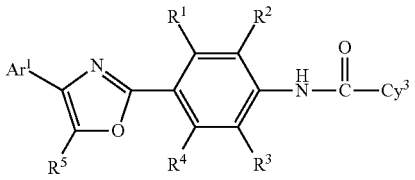

or a pharmaceutically acceptable salt thereof. In a further aspect, the compounds of the invention are represented by Formula IV

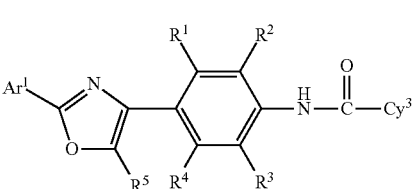

or a pharmaceutically acceptable salt thereof. In another aspect, the compounds of the invention are represented by Formula V

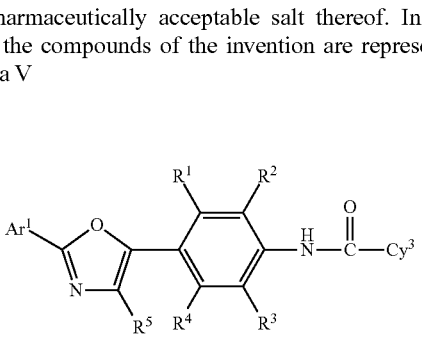

or a pharmaceutically acceptable salt thereof.

In one aspect, $R^5$ can be $C_{1-6}$alkyl or $C_{1-6}$haloalkyl in compounds of Formula I. In a further aspect, $R^5$ can be methyl or ethyl. In another aspect, $R^5$ can be trifluoromethyl.

The invention also provides compounds of Formula I or a pharmaceutically acceptable salt thereof, wherein $R^1$, $R^2$, $R^3$, and $R^4$ are each independently selected from H, $C_{1-6}$alkyl, $C_{1-6}$cycloalkyl, and $C_{1-6}$haloalkyl. In one aspect, $R^1$, $R^2$, $R^3$, and $R^4$ can each independently be H.

The invention also provides compounds of Formula I or a pharmaceutically acceptable salt thereof, wherein $Cy^3$ can be optionally substituted phenyl. In one aspect, the substituents can be independently selected from the group consisting of $C_{1-8}$alkyl, $C_{1-8}$alkenyl, $C_{1-8}$alkynyl, $C_{1-6}$haloalkyl, halogen, cyano and —$OR^c$. In another aspect, $Cy^3$ can be optionally substituted cyclohexyl.

The present invention encompasses the following compounds:

2-chloro-N-(4-(4-phenyl-5-(trifluoromethyl)oxazol-2-yl)phenyl)benzamide,
2-fluoro-4-methoxy-N-(4-(4-phenyl-5-(trifluoromethyl)oxazol-2-yl)phenyl)benzamide,
4-methoxy-N-(4-(4-phenyl-5-(trifluoromethyl)oxazol-2-yl)phenyl)benzamide,
4-fluoro-N-(4-(4-phenyl-5-(trifluoromethyl)oxazol-2-yl)phenyl)benzamide,
N-(4-(4-phenyl-5-(trifluoromethyl)oxazol-2-yl)phenyl)benzamide,
3-methyl-N-(4-(4-phenyl-5-(trifluoromethyl)oxazol-2-yl)phenyl)benzamide,
N-(4-(4-phenyl-5-(trifluoromethyl)oxazol-2-yl)phenyl)benzo[d][1,3]dioxole-5-carboxamide,
2-methyl-N-(4-(4-phenyl-5-(trifluoromethyl)oxazol-2-yl)phenyl)benzamide,
3-fluoro-N-(4-(4-phenyl-5-(trifluoromethyl)oxazol-2-yl)phenyl)benzamide,
2,4-dichloro-N-(4-(4-phenyl-5-(trifluoromethyl)oxazol-2-yl)phenyl)benzamide,
2-fluoro-N-(4-(4-phenyl-5-(trifluoromethyl)oxazol-2-yl)phenyl)benzamide,
2,4-difluoro-N-(4-(4-phenyl-5-(trifluoromethyl)oxazol-2-yl)phenyl)benzamide,
2-chloro-4-fluoro-N-(4-(4-phenyl-5-(trifluoromethyl)oxazol-2-yl)phenyl)benzamide,
3-chloro-N-(4-(4-phenyl-5-(trifluoromethyl)oxazol-2-yl)phenyl)benzamide,
3-methoxy-N-(4-(4-phenyl-5-(trifluoromethyl)oxazol-2-yl)phenyl)benzamide,
4-chloro-2-fluoro-N-(4-(4-phenyl-5-(trifluoromethyl)oxazol-2-yl)phenyl)benzamide,
4-ethyl-N-(4-(4-phenyl-5-(trifluoromethyl)oxazol-2-yl)phenyl)benzamide,
4-methyl-N-(4-(4-phenyl-5-(trifluoromethyl)oxazol-2-yl)phenyl)benzamide,
4-chloro-N-(4-(4-phenyl-5-(trifluoromethyl)oxazol-2-yl)phenyl)benzamide,
N-(4-(4-phenyl-5-(trifluoromethyl)oxazol-2-yl)phenyl)-4-(trifluoromethoxy)benzamide,
2-methoxy-N-(4-(4-phenyl-5-(trifluoromethyl)oxazol-2-yl)phenyl)benzamide,
N-(4-(4-phenyl-5-(trifluoromethyl)oxazol-2-yl)phenyl)isonicotinamide,
2,6-dichloro-N-(4-(4-phenyl-5-(trifluoromethyl)oxazol-2-yl)phenyl)benzamide,
N-(4-(4-phenyl-5-(trifluoromethyl)oxazol-2-yl)phenyl)-2-(trifluoromethyl)benzamide,
3-cyano-N-(4-(4-phenyl-5-(trifluoromethyl)oxazol-2-yl)phenyl)benzamide,
N-(4-(4-phenyl-5-(trifluoromethyl)oxazol-2-yl)phenyl)-3-(trifluoromethyl)benzamide,
N-(4-(4-phenyl-5-(trifluoromethyl)oxazol-2-yl)phenyl)cyclohexanecarboxamide,
4-cyano-N-(4-(4-phenyl-5-(trifluoromethyl)oxazol-2-yl)phenyl)benzamide,
4-(methylsulfonyl)-N-(4-(4-phenyl-5-(trifluoromethyl)oxazol-2-yl)phenyl)benzamide,
2-cyano-N-(4-(4-phenyl-5-(trifluoromethyl)oxazol-2-yl)phenyl)benzamide,
2,4-dichloro-N-(4-(5-methyl-4-phenyloxazol-2-yl)phenyl)benzamide,
2-chloro-N-(4-(5-methyl-4-phenyloxazol-2-yl)phenyl)benzamide,
2-chloro-N-(4-(5-methyl-2-phenyloxazol-4-yl)phenyl)benzamide,
2-chloro-N-(4-(4-(pyridin-4-yl)-5-(trifluoromethyl)oxazol-2-yl)phenyl)benzamide,
2,4-dichloro-N-(4-(2-phenyloxazol-4-yl)phenyl)benzamide,
2-chloro-N-(4-(2-phenyloxazol-4-yl)phenyl)benzamide,
N-(4-(4-(3-chlorophenyl)oxazol-2-yl)phenyl)benzamide,
2,4-dichloro-N-(4-(4-(3-chlorophenyl)oxazol-2-yl)phenyl)benzamide
2-chloro-N-(4-(4-(3-chlorophenyl)oxazol-2-yl)phenyl)benzamide
2-chloro-N-(4-(4-(2-chlorophenyl)oxazol-2-yl)phenyl)benzamide,
N-(4-(4-(2-chlorophenyl)oxazol-2-yl)phenyl)-4-methoxy-2-methylbenzamide,
2,6-dichloro-N-(4-(4-(2-chlorophenyl)oxazol-2-yl)phenyl)benzamide,
2,4-dichloro-N-(4-(4-(2-chlorophenyl)oxazol-2-yl)phenyl)benzamide,
N-(4-(4-(2-chlorophenyl)oxazol-2-yl)phenyl)-2-methylbenzamide,
N-(4-(4-(2-chlorophenyl)oxazol-2-yl)phenyl)benzamide,
2-chloro-N-(4-(4-(4-fluorophenyl)oxazol-2-yl)phenyl)benzamide,
2,4-dichloro-N-(4-(4-(4-fluorophenyl)oxazol-2-yl)phenyl)benzamide,
N-(4-(4-(4-fluorophenyl)oxazol-2-yl)phenyl)benzamide,
N-(2-methyl-4-(4-phenyloxazol-2-yl)phenyl)benzamide,
2,4-dichloro-N-(2-methyl-4-(4-phenyloxazol-2-yl)phenyl)benzamide,
2-chloro-N-(2-methyl-4-(4-phenyloxazol-2-yl)phenyl)benzamide,
N-(3-chloro-4-(4-phenyloxazol-2-yl)phenyl)benzamide,
2-chloro-N-(3-chloro-4-(4-phenyloxazol-2-yl)phenyl)benzamide,
2,4-dichloro-N-(3-chloro-4-(4-phenyloxazol-2-yl)phenyl)benzamide,
2-chloro-N-(4-(5-phenyloxazol-2-yl)phenyl)benzamide,
2-chloro-N-(4-(4-methyl-5-phenyloxazol-2-yl)phenyl)benzamide, and
2,4-dichloro-N-(4-(4-(2-chlorophenyl)-5-(trifluoromethyl)oxazol-2-yl)phenyl)benzamide,
or pharmaceutically acceptable salts thereof.

A. Preparation of Compounds

The present invention comprises processes for the preparation of compounds of Formula I.

Methods A-G below provide exemplary synthetic schemes for the preparation of the compounds of the present invention. One of skill in the art will understand that additional methods are also useful and that there are several ways to prepare the claimed compounds from commercially available starting materials using a variety of synthetic transformations and reagents.

Method A

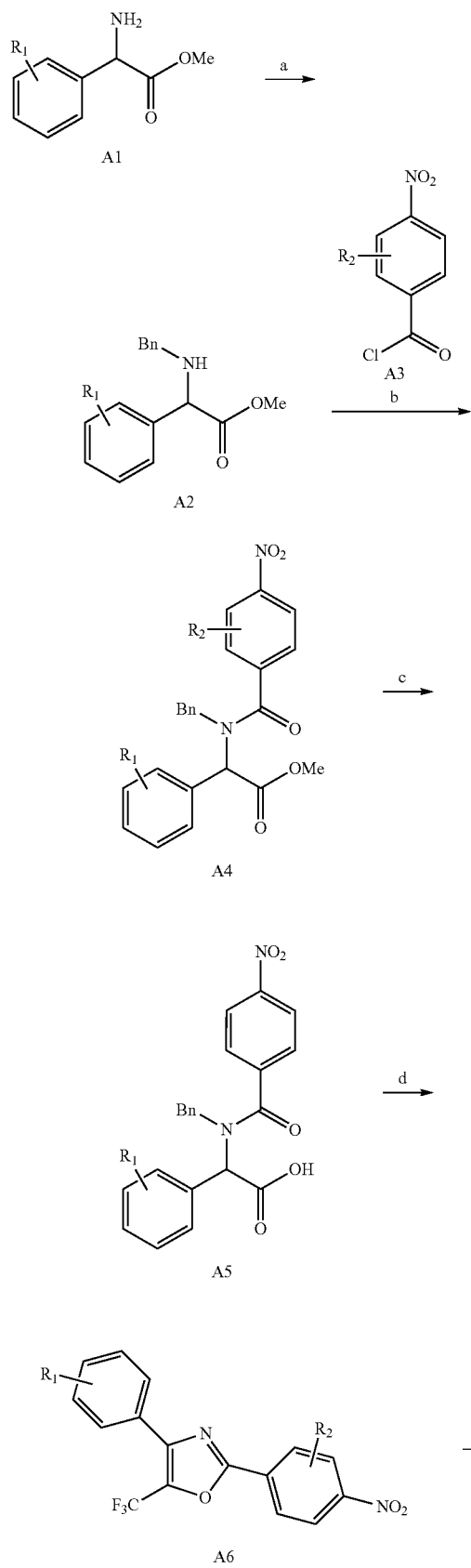

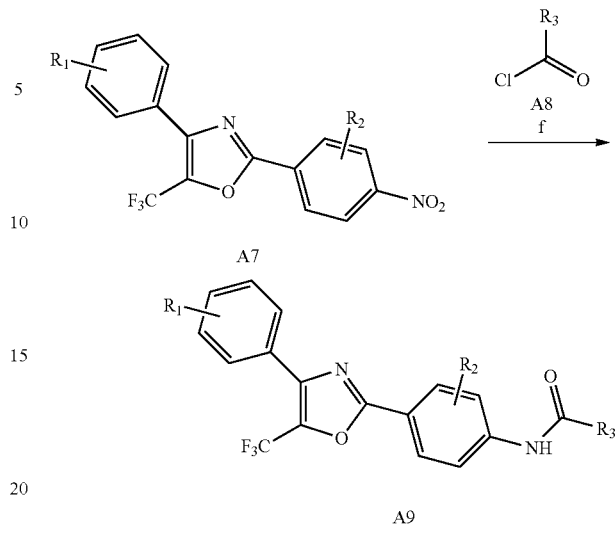

(a) PhCHO, NaBH(OAc)$_3$; (b) A3, pyridine; (c) LiOH, water; (d) TFAA, pyridine; (e) Zn, HOAc; (f) A8, pyridine Following a procedure described by Kawase et al. (*Heterocycles*, 1993, 36(11), 2441), oxazoles of the type A9 can be synthesized from readily available amino esters A1. The amino ester A1 may be N-benzylated by reductive amination with benzaldehyde, or alternatively by reaction with benzyl chloride and an appropriate base. The resulting secondary amine A2 is then acylated with a 4-nitrobenzoyl chloride A3, or a similarly activated 4-nitrobenzoyl group, to afford A4. This ester can be hydrolyzed to the acid under aqueous alkaline conditions and the resulting acid A5 transformed to the oxazole A6 following the procedure described by Kawase et al. using trifluoroacetic anhydride and pyridine in refluxing toluene. Reduction of the aryl nitro group in A6 to the aryl amine A7 is accomplished with zinc in acetic acid, though iron in acetic acid, catalytic hydrogenation or tin (II) chloride can also be used to effect this reduction. Lastly, the aryl amine A7 is reacted with an acid chloride A8, or a similarly activated acid derivative, to afford the final product A9.

Method B

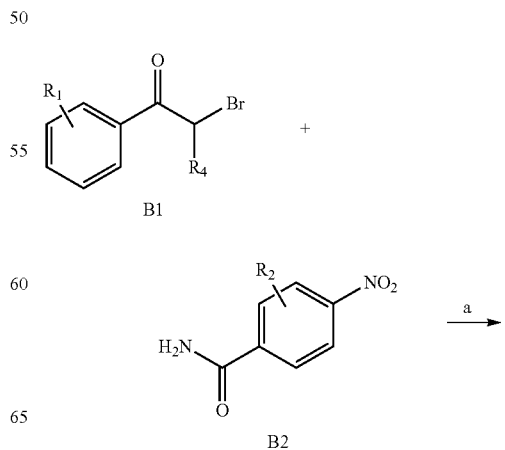

-continued

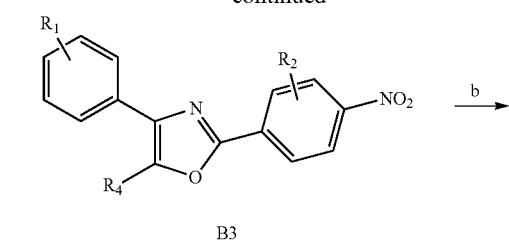

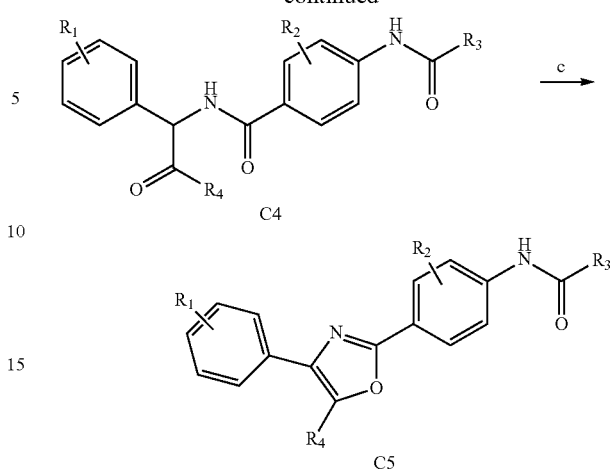

(a) EDC, HOBT, DMF; (b) Dess-Martin periodinane; (c) POCl₃

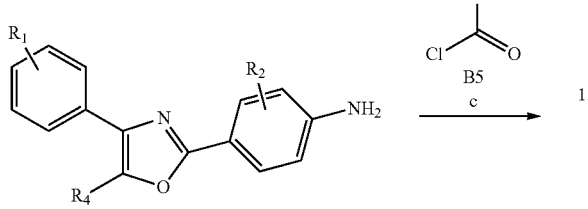

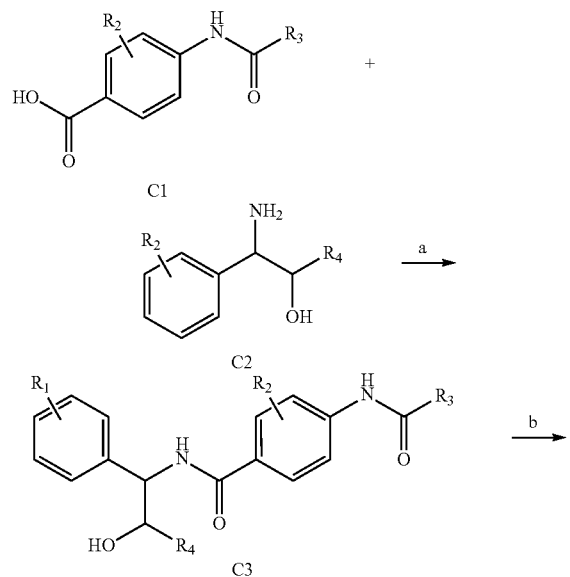

(a) 135° C., NMP; (b) Zn, HOAc; (c) B5, pyridine

The oxazole B3 can be prepared from a phenacyl bromide B1 and a 4-nitrobenzamide B2 by heating in a minimum volume of NMP at 135° C. following a procedure similar to that described by Hammar et al. (*J. Heterocyclic Chem.* 1981, 18(5), 885). Reduction of aryl nitro B3 followed by reaction with acid chloride B5 can be carried out in the manner described for steps e and f in Method A to afford final product B6.

Method C

Method C describes the synthetic sequence to final product C5. From the coupling of readily available benzoic acids C1 and amino alcohols C2 via common peptide bond forming transformations the amido alcohol C3 can be formed. The alcohol is conveniently oxidized to the ketone C4 with Dess-Martin periodinane or any of a variety of other oxidizing agents, e.g. TPAP or Swern conditions. The desired oxazole C5 is formed via a Robinson-Gabriel cyclodehydration using phosphorous oxychloride. This procedure is well-precedented and has been used by, for example, R. L. Dow (*J. Org. Chem.* 1990, 55(1), 386).

Method D

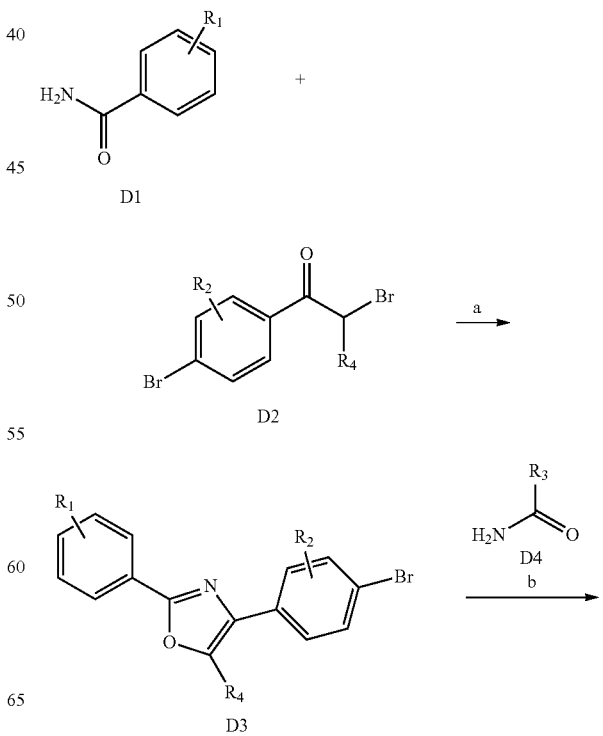

17

-continued

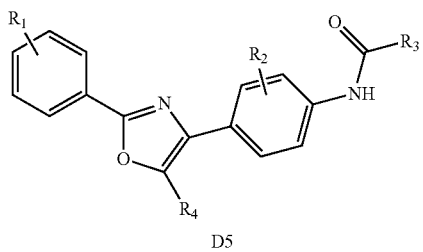

D5

(a) NMP 135° C.; (b) D4 cat. CuI, K₂CO₃, N,N'-dimethylethylenediamine

Method D is a variation of Method B wherein the benzamide D1 bears the R₁-substituted phenyl ring and the phenacyl bromide D2 bears the R₂-substituted phenyl ring. The conditions for formation of the oxazole D3 are identical to those of Method B. Then N-arylation of the amide D4 with aryl bromide D3 affords the fully elaborated oxazole D5.

Method E

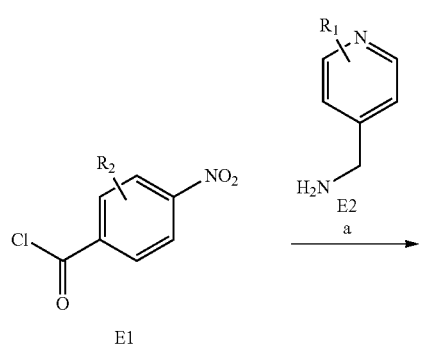

18

-continued

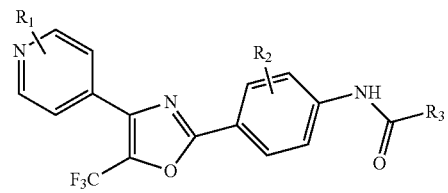

E7

(a) E2, pyridine; (b) trifuoroacetic anhydride, pyridine; (c) H₂, Pd on carbon; (d) E6 pyridine Oxazole E7 can be synthesized from readily available starting materials E1 and E2 following a procedure described by Brana et al. (*Synthesis* 2003, (14), 2211). It should be recognized by one skilled in the art of organic synthesis that the peptide bond-forming reaction between E1 and E2 in step a can be accomplished by a number of methods utilizing activated derivatives of E1 with a variety of reagents, e.g. EDC, HOBT, to form E3. The oxazole-forming step follows Brana's experimental procedure to afford E4. Reduction of the aryl nitro group to the aryl amine E5 is effected using zinc in acetic acid, though there are a number of synthetic transformations that can reduce the nitro group, e.g. iron in acetic acid, palladium-catalyzed hydrogenation and tin (II) chloride. Lastly the amide bond-forming reaction in step d is conveniently executed by combining acid chloride E6 with aniline E5 to generate the final product E7. This transformation may be accomplished using alternative synthetic methods as described in the reaction of E1 and E2 above.

Method F

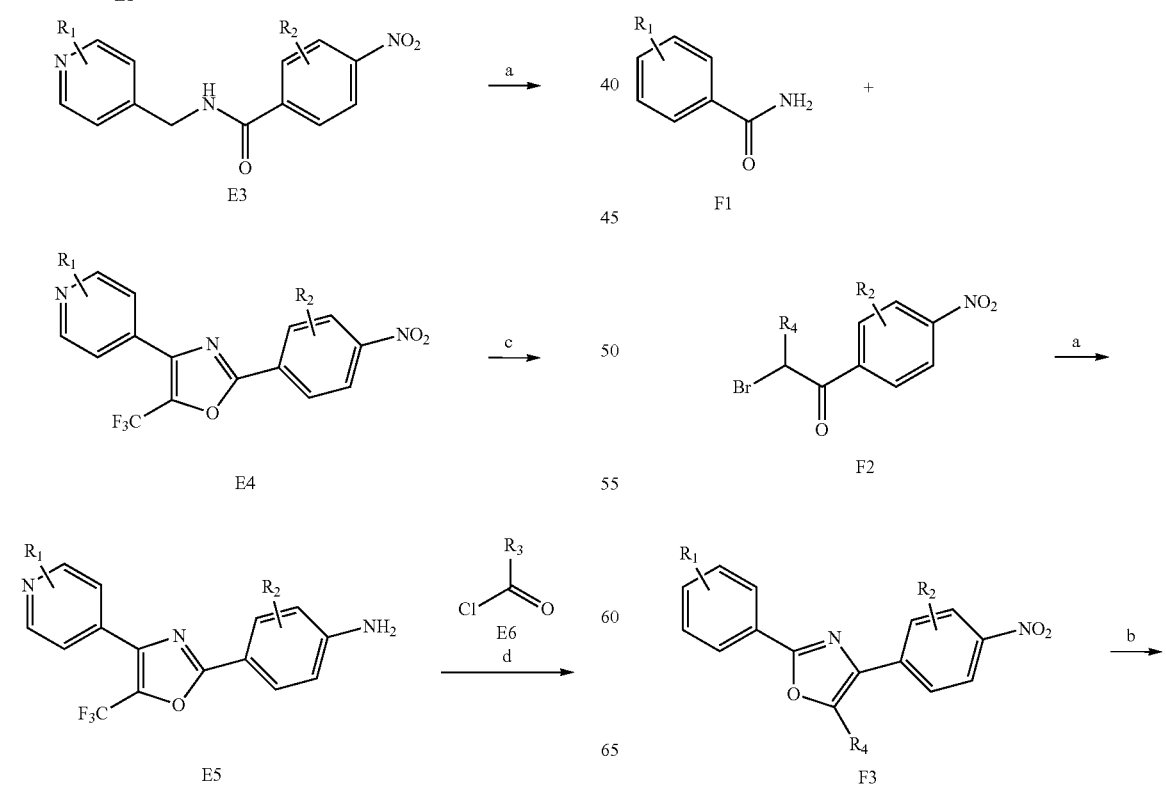

-continued

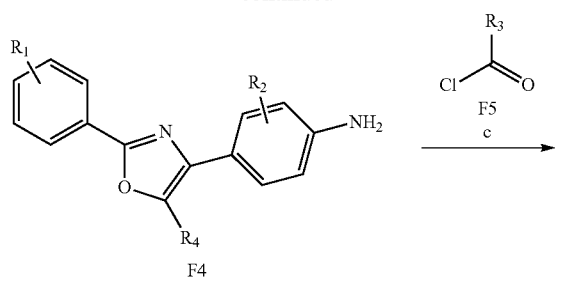

F4

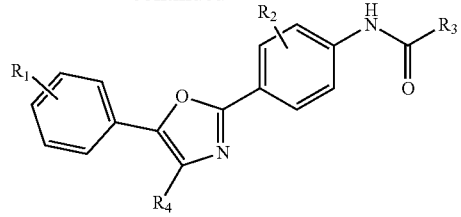

G6

(a) pyridine; (b) pyridine; (c) i. Dess-Martin periodinane, ii. POCl₃

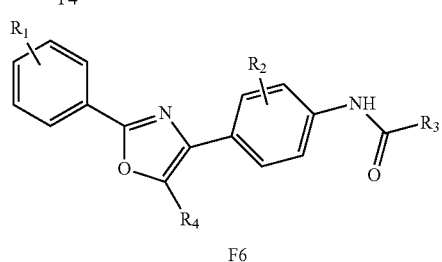

F6

(a) NMP, 135° C.; (b) Zn, HOAc; (c) F5, pyridine

General synthetic Method F follows a sequence similar to that described in Method B. Benzamide F1 is combined with phenacyl bromide F2 to afford the oxazole F3 with heat in a minimum volume of NMP. The aryl nitro group in F3 is reduced to the corresponding aniline F4 using zinc in acetic acid though there are several alternative reduction methods as previously described. Lastly, the amide bond in final product F6 is formed by reaction of F4 with an acid chloride F5, and there are several alternative coupling methods to effect this transformation as previously described.

Method G

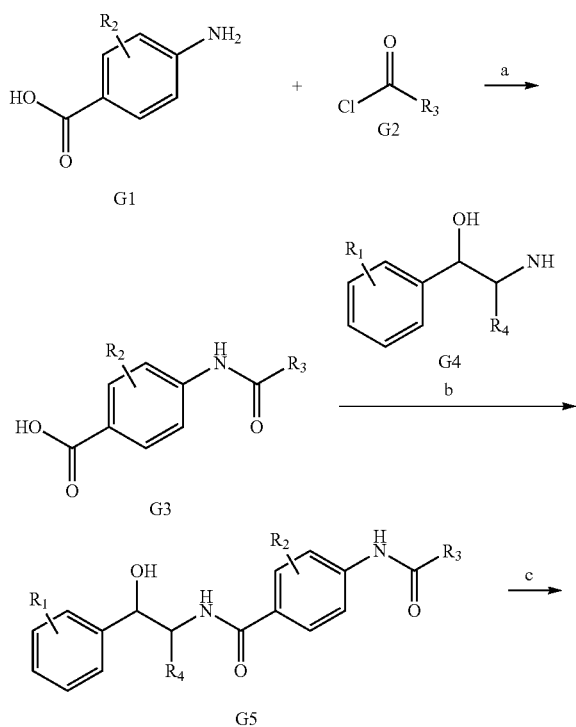

According to Method G, formation of the final product G6 can be accomplished from readily available starting materials G1 and G2 following a synthetic sequence similar to that described in Method C. Sequential amide bond formations in steps a and b afford alcohol G5 via benzoic acid G3. The Robinson-Gabriel oxazole synthesis of final product G6 is accomplished by oxidation of the alcohol G5 to the corresponding ketone followed by cyclodehydration using a dehydrating reagent such as phosphorous oxychloride.

B. Pharmaceutical Compositions and Administration

Compounds useful in the present invention can be used in the form of pharmaceutically acceptable salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, mandelate, methansulfonate, nicotinate, 2-naphthalenesulfonate, oxalate, palmoate, pectinate, persulfate, 2-phenylpropionate, picrate, pivalate, propionate, salicylate, succinate, sulfate, tartrate, thiocyanate, tosylate, mesylate, and undecanoate. When compounds of the invention include an acidic function such as a carboxy group, then suitable pharmaceutically acceptable salts for the carboxy group are well known to those skilled in the art and include, for example, alkaline, alkaline earth, ammonium, quaternary ammonium cations and the like. For additional examples of "pharmacologically acceptable salts," see infra and Berge et al. *J. Pharm. Sci.* 66: 1, 1977. In certain embodiments of the invention salts of hydrochloride and salts of methanesulfonic acid can be used.

For administration, the compounds useful in this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds useful in this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

The therapeutically effective amount of the smoothed receptor modulator in the compositions useful in the invention can range from about 0.1 mg to about 180 mg, for example from about 5 mg to about 180 mg, or from about 1 mg to about 100 mg of the smoothened antagonist per subject. In some aspects, the therapeutically effective amount of the compound in the composition can be chosen from about 0.1 mg, about 1 mg, 5 mg, about 15 mg, about 20 mg, about 30 mg, about 50 mg, about 60 mg, about 75 mg, about 90 mg, about 120 mg, about 150 mg, about 180 mg.

While it may be possible to administer a compound of the invention to a subject alone, the compound administered will normally be present as an active ingredient in a pharmaceutical composition. Thus, a pharmaceutical composition of the invention may comprise a therapeutically effective amount of at least one smoothed receptor modulator compound, or an effective dosage amount of at least one smoothed receptor modulator compound.

As used herein, an "effective dosage amount" is an amount that provides a therapeutically effective amount of the smoothened antagonist when provided as a single dose, in multiple doses, or as a partial dose. Thus, an effective dosage amount of the smoothened antagonist of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multidose pharmaceutical composition, such as powders, liquids and the like, in which an effective amount of the smoothed receptor modulator compound is administered by administering a portion of the composition.

Alternatively, a pharmaceutical composition in which two or more unit dosages, such as in tablets, capsules and the like, are required to administer an effective amount of the smoothed receptor modulator may be administered in less than an effective amount for one or more periods of time (e.g., a once-a-day administration, and a twice-a-day administration), for example to ascertain the effective dose for an individual subject, to desensitize an individual subject to potential side effects, to permit effective dosing readjustment or depletion of one or more other therapeutics administered to an individual subject, and/or the like.

The effective dosage amount of the pharmaceutical composition useful in the invention can range from about 1 mg to about 360 mg from a unit dosage form, for example about 5 mg, about 15 mg, about 30 mg, about 50 mg, about 60 mg, about 75 mg, about 90 mg, about 120 mg, about 150 mg, about 180 mg, about 210 mg, about 240 mg, about 300 mg, or about 360 mg from a unit dosage form.

III. Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "combination-therapy", in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneously with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents, which may be used in combination with compounds of the present invention, consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents, which may be used in combination with compounds of the present invention, consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit anti-thymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), VECTIBIX™ (panitumumab), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., US Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., US Publication No. 2002/0042368), specifically binding anti-eph receptor and/or anti-ephrin antibodies or antigen binding regions (U.S. Pat. Nos. 5,981,245; 5,728,813; 5,969, 110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, KDR inhibitors, EGF inhibitors and CDK inhibitors, TNF inhibitors, metallomatrix proteases inhibitors (MMP), COX-2 inhibitors including celecoxib, NSAID's, or $\alpha_v\beta_3$ inhibitors.

IV. Therapeutic Uses of the Compounds of the Invention

Compounds and compositions of the present application may thus be used, in one aspect, for the treatment or prevention of angiogenesis related diseases. "Angiogenesis" refers to any alteration of an existing vascular bed or the formation of new vasculature, which benefits tissue perfasion. This includes the formation of new vessels by sprouting of endothelial cells from existing blood vessels or the remodelling of existing vessels to alter size, maturity, direction or flow properties to improve blood perfusion of tissue.

Hh is known to stimulate angiogenesis. It has been demonstrated that Matrigel plugs impregnated with hedgehog protein and inserted into mice evince substantial neovascularization, whereas Matrigel plugs not carrying hedgehog show comparatively little vascularization. Hedgehog protein is also capable of increasing vascularization of the normally avascular mouse cornea. The PTCH1 gene is expressed in normal vascular tissues, including the endothelial cells of the aorta, vascular smooth muscle cells, adventitial fibroblasts of the aorta, the coronary vasculature and cardiomyocytes of the atria and ventricles. These tissues are also sensitive to hedgehog protein. Treatment with exogenous hedgehog causes upregulation of PTCH1 expression. In addition, hedgehog proteins have been shown to stimulate proliferation of vascular smooth muscle cells in vivo. Hedgehog proteins also cause fibroblasts to increase expression of angiogenic growth factors such as VEGF, bFGF, Ang-1 and Ang-2. Lastly, hedgehog proteins are known to stimulate recovery from ischemic injury and stimulate formation of collateral vessels. Given that Hh promotes angiogenesis, antagonists of Hh pathway, such as SMO antagonists of the present invention are useful as angiogenesis inhibitors, particularly in situations where some level of hedgehog signaling is necessary for angiogenesis.

Angiogenesis is fundamental to many disorders. Persistent, unregulated angiogenesis occurs in a range of disease states, tumor metastases and abnormal growths by endothelial cells. The vasculature created as a result of angiogenic processes supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

The compounds and compositions of the current invention can be used to treat diseases supported by or associated with angiogenesis. These diseases include ocular neovascular disease, age-related macular degeneration, diabetic retinopathy, retinopathy of prematurity, corneal graft rejection, neovascular glaucoma, retrolental fibroplasia, epidemnic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, corneal graph rejection, rheumatoid arthritis, osteoarthritis chronic inflammation (e.g., ulcerative colitis or Crohn's disease), hemangioma, Osler-Weber-Rendu disease, and hereditary hemorrhagic telangiectasia.

In addition, angiogenesis plays a critical role in cancer. A tumor cannot expand without a blood supply to provide nutrients and remove cellular wastes. Tumors in which angiogenesis is important include solid tumors such as rhabdomyosarcomas, retinoblastoma, Ewing sarcoma, neuroblastoma, and osteosarcoma, and benign tumors such as acoustic neuroma, neurofibroma, trachoma and pyogenic granulomas. Angiogenic factors have been found associated with several solid tumors. Prevention of angiogenesis could halt the growth of these tumors and the resultant damage to the animal due to the presence of the tumor. Angiogenesis is also associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

In addition to tumor growth, angiogenesis is important in metastasis. Initially, angiogenesis is important in the vascularization of the tumor which allows cancerous cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

It is further contemplated that the use of the smoothened antagonists of the present invention may be specifically targeted to disorders where the affected tissue and/or cells evince high Hh pathway activation. Expression of GLI genes is activated by the hedgehog signaling pathway, including GLI1, GLI2 and GLI3. GLI1 expression is most consistently correlated with hedgehog signaling activity across a wide range of tissues and disorders, while GLI3 is somewhat less so. The GLI genes encode transcription factors that activate expression of many genes needed to elicit the full effects of Hh signaling. However, the GLI3 transcription factor can also act as a repressor of hedgehog effector genes, and therefore, expression of GLI3 can cause a decreased effect of the hedgehog signaling pathway. Whether GLI3 acts as a transcriptional activator or repressor depends on post-translational events, and therefore it is expected that methods for detecting the activating form (versus the repressing form) of GLI3 protein would also be a reliable measure of hedgehog pathway activation. GLI2 gene expression is expected to provide a reliable marker for Hh pathway activation. The GLI1 gene is strongly expressed in a wide array of cancers, hyperplasias and immature lungs, and serves as a marker for the relative activation of the hedgehog pathway. In addition, tissues, such as immature lung, that have high GLI gene expression are strongly affected by hedgehog inhibitors. Accordingly, it is contemplated that the detection of GLI gene expression may be used as a powerful predictive tool to identify tissues and disorders that will particularly benefit from treatment with an antagonist of Hh pathway.

In one aspect, GLI1 expression levels can be detected, either by direct detection of the transcript or by detection of protein levels or activity. Transcripts may be detected using any of a wide range of techniques that depend primarily on hybridization of probes to the GLI1 transcripts or to cDNAs synthesized therefrom. Well-known techniques include Northern blotting, reverse-transcriptase PCR and microarray analysis of transcript levels. Methods for detecting GLI protein levels include Western blotting, immunoprecipitation, two-dimensional polyacrylamide gel electrophoresis (2D SDS-PAGE) (for example, compared against a standard wherein the position of the GLI proteins has been determined), and mass spectroscopy. Mass spectroscopy may be coupled with a series of purification steps to allow high-throughput identification of many different protein levels in a particular sample. Mass spectroscopy and 2D SDS-PAGE can also be used to identify post-transcriptional modifications to proteins including proteolytic events, ubiquitination, phosphorylation, lipid modification etc. GLI activity may also be assessed by analyzing binding to substrate DNA or in vitro transcriptional activation of target promoters. Gel shift assays, DNA footprinting assays and DNA-protein crosslinking assays are all methods that may be used to assess the presence of a protein capable of binding to GLI binding sites on DNA. (*J Mol Med* 1999; 77(6):459-68; *Cell* 2000 Feb. 18; 100(4): 423-34; *Development* 2000; 127(19):4293-4301).

In another aspect, GLI transcript levels are measured and diseased or disordered tissues showing abnormally high GLI levels are treated with a hedgehog antagonist. Premature lung tissue, lung cancers (e.g., adenocarcinomas, broncho-alveolar adenocarcinomas, small cell carcinomas), breast cancers (e.g., inferior ductal carcinomas, inferior lobular carcinomas, tubular carcinomas), prostate cancers (e.g., adenocarcinomas), pancreatic adenocarcinomas, gastric cancers, and benign prostatic hyperplasias all show strongly elevated GLI1 expression levels in certain cases. Accordingly, GLI1 expression levels are a powerful diagnostic device to determine which of these tissues should be treated with a smoothened antagonist. In addition, there is substantial correlative evidence that cancers of urothelial cells (e.g., bladder cancer, other urogenital cancers) will also have elevated GLI1 levels in certain cases. For example, it is known that loss of heterozygosity on chromosome 9q22 is common in bladder cancers. The ptc-1 gene is located at this position and ptc-1 loss of function is probably a partial cause of hyperproliferation, as in many other cancer types. Accordingly, such cancers would also show high GLI expression and would be particularly amenable to treatment with a smoothened antagonist.

It is anticipated that any degree of GLI overexpression may be useful in determining that a smoothened antagonist will be an effective therapeutic. In one aspect, GLI should be expressed at a level at least twice as high as normal.

The compounds and compositions of the present invention can be used in the treatment of neoplastic or hyperplastic transformations such as may occur in the central nervous system. For instance, the smoothened antagonists can be utilized to cause such transformed cells to become either post-mitotic or apoptotic. The present method may, therefore, be used as part of a treatment for, e.g., malignant gliomas, meningiomas, medulloblastomas, neuroectodermal tumors, and ependymomas. In one aspect, the subject method can be used as part of a treatment regimen for malignant medulloblastoma and other primary CNS malignant neuroectodermal tumors.

In another aspect, the methods of the invention can be used as part of treatment program for medulloblastoma. These tumors are also referred to as primitive neuroectodermal tumor (PNET). Medulloblastoma, a primary brain tumor, is the most common brain tumor in children. It is a primitive neuroectodermal tumor arising in the posterior fossa. Medulloblastomas account for approximately 25% of all pediatric brain tumors. Histologically, they are small round cell tumors commonly arranged in true rosettes, but may display some differentiation to astrocytes, ependymal cells or neurons. They may arise in other areas of the brain including the pineal gland (pineoblastoma) and cerebrum. Those arising in the supratentorial region generally fare worse than their counterparts. Medulloblastoma/PNETs are known to recur anywhere in the CNS after resection, and can even metastasize to bone. Pretreatment evaluation should therefore include an examination of the spinal cord to exclude the possibility of "dropped metastases". Gadolinium-enhanced MRI has largely replaced myelography for this purpose, and CSF cytology is obtained postoperatively as a routine procedure.

In other aspects, the smoothened antagonists of the invention can be used as part of treatment program for ependymomas. Ependymomas account for approximately 10% of the pediatric brain tumors in children. Grossly, they are tumors that arise from the ependymal lining of the ventricles and microscopically form rosettes, canals, and perivascular rosettes. In 51 children reported with ependymomas, ¾ were histologically benign. Approximately ⅔ arose from the region of the 4th ventricle. One third presented in the supratentorial region. Age at presentation peaks between birth and 4 years. The median age is about 5 years. Because so many children with this disease are babies, they often require multimodal therapy.

It has been reported that Sonic hedgehog regulates lung mesenchymal cell proliferation in vivo. Accordingly, methods of the present invention can be used to regulate regeneration of lung tissue, e.g., in the treatment of emphysema. It has also been demonstrated that Sonic hedgehog is expressed in human lung squamous carcinoma and adenocarcinoma cells. Fujita et al. (1997) *Biochem Biophys Res Commun* 238: 658. The expression of Sonic hedgehog was also detected in the human lung squamous carcinoma tissues, but not in the normal lung tissue of the same patient. They also observed that Sonic hedgehog stimulates the incorporation of BrdU into the carcinoma cells and stimulates their cell growth, while anti-Shh-antibody inhibited their cell growth. These results suggest that Hh, and/or SMO is involved in the cell growth of such transformed lung tissue and therefore indicate that the smoothened antagonists of the invention can be used as part of a treatment of lung carcinoma and adenocarcinomas, and other proliferative disorders involving the lung epithelia.

BCC is the most common human cancer, accounting for about 70% of human skin cancers, and representing at least one third of all cancer diagnosed in the US each year. More than 99% of BCC cases arise sporadically in the population, with only 0.5% of cases arising in individuals with Gorlin's Syndrome (GS). BCC rarely metastasizes, but can be locally aggressive and recurrent. Inactivating mutations in PTCH1 occur most commonly in these tumors. A subset of BCC is driven via mutations in SMO, and these mutations activate the pathway by generating proteins with decreased sensitivity to PTCH1 suppression. In one aspect, the methods of the current invention can be used for treatment of BCC.

Hh pathway has been implicated in many other types of cancer, including pancreatic cancer, other tumors of the gastrointestinal (GI) tract and prostate cancer. Abnormal expression of SHH, PTCH1 and SMO has been shown early in the formation of human pancreatic tumors. Thayer, S. P. et al. (2003) *Nature* 425: 313-317. Several pancreatic cancer cell lines were found to be PTCH1 and SMO-positive and growth inhibited in vitro by cyclopamine, suggesting an active autocrine loop through which tumor cells both make and respond to Hh ligand. Furthermore, systemic treatment with cyclopamine slowed the growth of tumors formed by these cell lines when implanted into nude mice. Similar observations were made for pancreatic and other GI tumors. Berman, D. M. et al. (2003) Nature 425: 846-851. Similar data was provided for prostate cancer as well, including SHH overexpression in tumor biopsies, especially in higher Gleason grade tumors, and in vitro and in vivo inhibitory effects of cyclopamine on growth of prostate cancer cell lines. The Hh pathway was further implicated in prostate tumor metastasis, as the capacity of AT6.3 cells to metastasize to the lung was completely abrogated by cyclopamine, and AT2.1, a rarely metastasizing clone, could be induced to metastasize by overexpression of GLI1, in a cyclopamine-insensitive manner. Thus, the smoothened antagonists of the invention can be used for the treatment of pancreatic and prostatic cancers.

Many other tumors may, based on evidence such as involvement of the Hh pathway in these tumors, or detected expression of hedgehog or its receptor in these tissues during development, be affected by treatment with the subject compounds. Such tumors include, but are by no means limited to, tumors related to Gorlin's syndrome (e.g., medulloblastoma, meningioma, etc.), tumors evidenced in PTCH1 knock-out mice (e.g., hemangioma, rhabdomyosarcoma, etc.), tumors resulting from GLI1 amplification (e.g., glioblastoma, sarcoma, etc.), tumors connected with TRC8, a PTCH1 homolog (e.g., renal carcinoma, thyroid carcinoma, etc.), Ext-1-related tumors (e.g., bone cancer, etc.), Shh-induced tumors (e.g., lung cancer, chondrosarcomas, etc.), and other tumors (e.g., breast cancer, urogenital cancer (e.g., kidney, bladder, ureter, prostate, etc.), adrenal cancer, and gastrointestinal cancer (e.g., stomach, intestine, etc.).

Further, the pharmaceutical preparations of the invention can be used for the treatment of hyperplastic epidermal conditions, such as keratosis, as well as for the treatment of neoplastic epidermal conditions such as those characterized by a high proliferation rate for various skin cancers, as for example squamous cell carcinoma. The subject method can also be used in the treatment of autoimmune diseases affecting the skin, in particular, of dermatological diseases involving morbid proliferation and/or keratinization of the epidermis, as for example, caused by psoriasis or atopic dermatosis.

Besides being useful for human treatment, these compounds are also useful for veterinary treatment of companion animals, exotic animals and farm animals, including mammals, rodents, and the like. Examples include horses, dogs, and cats.

As used herein, the compounds of the present invention include the pharmaceutically acceptable derivatives thereof.

The present invention, thus generally described, will be understood more readily by reference to the following examples, which are provided by way of illustration and are not intended to be limiting of the present invention. Compounds of the invention may be synthesized from simple starting molecules and commercially available materials as illustrated in the Examples. Various modifications of the invention in addition to those shown and described herein will become apparent to those skilled in the art and are intended to fall within the scope of the appended claims. To this end, it should be noted that one or more hydrogen atoms or methyl groups may be omitted from the drawn structures consistent with accepted shorthand notation of such organic compounds, and that one skilled in the art of organic chemistry would readily appreciate their presence. The structure of the prepared compounds is verified by mass spectral data. For some compounds, ions having mass greater than M+H are reported. These ions generally represent dimers or trimers of the synthesized compound, and in some instances represent trifluoroacetate adducts generated from the mobile phase of the LC/MS. The trifluoroacetate adducts will have a weight of M+115.

Example 1

Compound 1 was synthesized following synthetic method A as shown in Scheme 1.

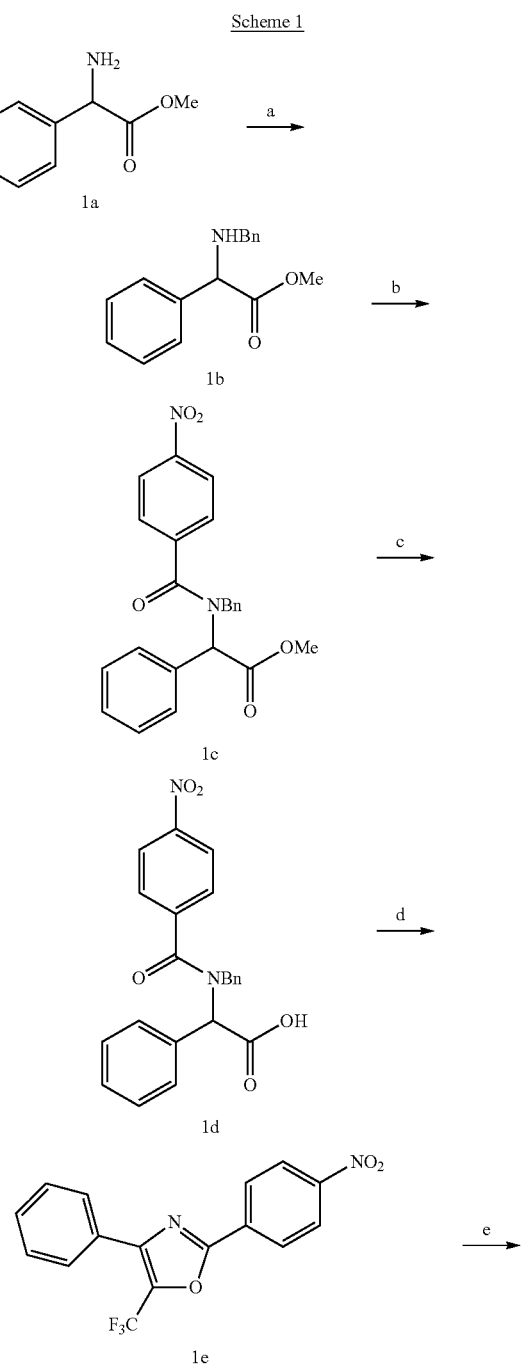

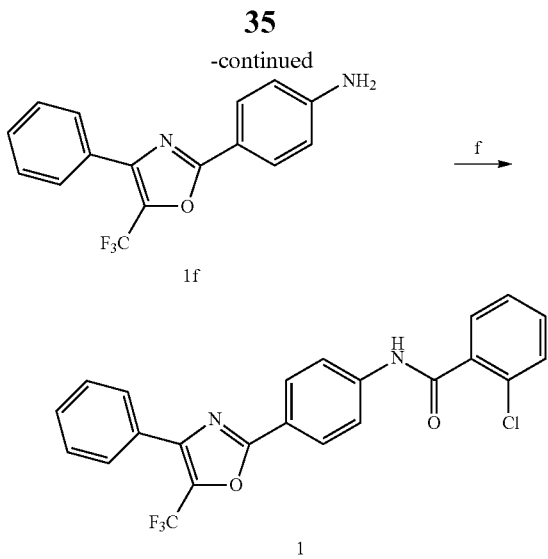

(a) benzaldehyde, sodium triacetoxyborohydride, 1,2-dichloroethane, room temperature; (b) 4-nitrobenzoylchloride, pyridine, dichloromethane, room temperature; (c) lithium hydroxide, water, methanol, tetrahyrofuran, room temperature; (d) trifluoroacetic anhydride, pyridine, toluene, reflux; (e) zinc, acetic acid, room temperature; (f) 2-chlorobenzoyl chloride, pyridine, dichloromethane, room temperature.

Preparation of methyl 2-(benzylamino)-2-phenylacetate (1b): to a mixture of benzaldehyde (3.06 ml, 30.3 mmol) and methyl 2-amino-2-phenylacetate 1a (4.552 g, 27.6 mmol) in 50 mL 1,2-dichloroethane was added sodium triacetoxyborohydride (14.6 g, 68.9 mmol) all at once. The reaction mixture was stirred at room temperature for several hours then poured into 100 mL saturated aqueous sodium bicarbonate solution. The biphase was vigorously stirred for 15 minutes then the organic separation dried over magnesium sulfate, filtered and the filtrate concentrated under reduced pressure to afford a colorless oil. The product was purified by chromatography on silica gel eluting with 10-40% ethyl acetate in hexane. ESI$^+$ m/z=256.1 [MH]$^+$.

Preparation of methyl 2-(N-benzyl-4-nitrobenzamido)-2-phenylacetate (1c): to a solution of methyl 2-(benzylamino)-2-phenylacetate (4.818 g, 18.9 mmol) and pyridine (15.3 ml, 189 mmol) in 75 mL dichloromethane cooled by an ice bath was added 4-nitrobenzoyl chloride (3.50 g, 18.9 mmol) all at once. The cold bath was removed and the reaction stirred to room temperature. The reaction was stirred at room temperature for four hours then concentrated under reduced pressure, taken up in 100 mL heptane and concentrated under reduced pressure. The concentrate was partitioned between 100 mL dichloromethane and 100 mL water. The organic separation was washed with 50 mL brine then stirred over magnesium sulfate, filtered and the filtrate concentrated under reduced pressure to afford a colorless oil. The product was purified by chromatography on silica, eluting with 10-30% ethyl acetate in hexane to afford a colorless foamy solid (7.37 g, 96%). ESI$^+$ m/z=405.1 [MH]$^+$.

Preparation of 2-(N-benzyl-4-nitrobenzamido)-2-phenylacetic acid (1d): to a room temperature solution of methyl 2-(N-benzyl-4-nitrobenzamido)-2-phenylacetate (7.63 g, 18.9 mmol) dissolved in 40 mL methanol and 30 mL THF was added a solution of lithium hydroxide monohydrate (1.95 g, 46.5 mmol) dissolved in 15 mL water. The solution turned dark brown and gradually turned light orange over 15 minutes. After 30 minutes the solvent was removed under reduced pressure and the concentrate was diluted with 50 mL water and extracted with 2×50 mL dichloromethane. The organic extracts were combined and washed with 50 mL brine then stirred over magnesium sulfate, filtered and the filtrate concentrated under reduced pressure to afford a colorless foamy solid (7.30 g, 99%). ESI$^-$ m/z=779.2 [2M–H]$^-$.

Preparation of 2-(4-nitrophenyl)-4-phenyl-5-(trifluoromethyl)oxazole (1e): to a solution of bis(trifluoroacetic) anhydride (3.1 ml, 22 mmol) and pyridine (3.5 ml, 44 mmol) in 30 mL benzene cooled by an ice bath was added 2-(N-benzyl-4-nitrobenzamido)-2-phenylacetic acid (2.852 g, 7.3 mmol). The reaction was equilibrated to room temperature for several hours then heated to reflux. The reaction was left stirring at reflux overnight. After ca. 16 h the reaction was poured into 100 mL saturated aqueous sodium bicarbonate solution. The aqueous layer was extracted with 2×50 mL ethyl acetate. Combined organic layers were washed with 50 mL brine then stirred over magnesium sulfate, filtered and the filtrate concentrated under reduced pressure to afford a red oil. The product was isolated by chromatography on silica gel, eluting with 15-40% ethyl acetate in hexanes, to afford purified product as a colorless, crystalline solid (1.5 g 61%). ESI$^+$ m/z=335.0 [MH]$^+$.

Preparation of 4-(4-phenyl-5-(trifluoromethyl)oxazol-2-yl)benzenamine (1f): to a solution of 2-(4-nitrophenyl)-4-phenyl-5-(trifluoromethyl)oxazole (437 mg, 1307 µmol) in 20 mL acetic acid at room temperature was added zinc dust (1282 mg, 19611 µmol) all at once. An exotherm resulted. The mixture was stirred at room temperature for 2 hours then filtered. The filtrate was concentrated under reduced pressure, taken up in 25 mL toluene and concentrated under reduced pressure again to afford a yellow, foamy solid (350 mg, 88%). ESI$^+$ m/z=305.0 [MH]$^+$.

Preparation of 2-chloro-N-(4-(4-phenyl-5-(trifluoromethyl)oxazol-2-yl)phenyl)benzamide (1): to a solution of 4-(4-phenyl-5-(trifluoromethyl)oxazol-2-yl)benzenamine (178 mg, 585 µmol) and pyridine (473 µl, 5850 µmol) in 5 mL dichloromethane at room temperature was added 2-chlorobenzoyl chloride (78.0 µl, 614 µmol) all at once by pipet. After one hour the reaction was concentrated under reduced pressure then taken up in 25 mL dichloromethane and washed with 25 mL saturated aqueous sodium bicarbonate solution. The organic separation was stirred over magnesium sulfate, filtered and the filtrate concentrated under reduced pressure to afford a yellow oil. The product was isolated by chromatography on silica gel, eluting with 15-40% ethyl acetate in hexane, to yield a colorless foamy solid (213 mg, 82%). ESI$^+$ m/z=443.0 [MH]$^+$.

Examples 2-30

Compounds 2-30 were synthesized in a similar fashion to Example 1 following general synthetic Method A by reacting intermediate 1f with the appropriate acid chloride to afford the corresponding amide product examples 2-30 shown below in Table 1.

TABLE 1

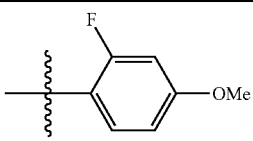

| Example | Compound Name | Ar | MH+ |
|---|---|---|---|
| 2 | 2-fluoro-4-methoxy-N-(4-(4-phenyl-5-(trifluoromethyl)oxazol-2-yl)phenyl)benzamide | 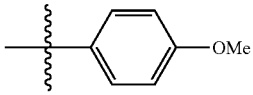 | 457.1 |
| 3 | 4-methoxy-N-(4-(4-phenyl-5-(trifluoromethyl)oxazol-2-yl)phenyl)benzamide | 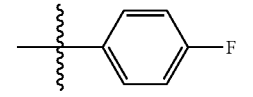 | 439.1 |
| 4 | 4-fluoro-N-(4-(4-phenyl-5-(trifluoromethyl)oxazol-2-yl)phenyl)benzamide | 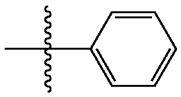 | 427.0 |
| 5 | N-(4-(4-phenyl-5-(trifluoromethyl)oxazol-2-yl)phenyl)benzamide | 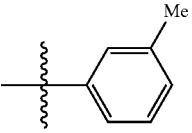 [SMILES: *c1cccc(C)c1] | 409.1 |
| 6 | 3-methyl-N-(4-(4-phenyl-5-(trifluoromethyl)oxazol-2-yl)phenyl)benzamide | 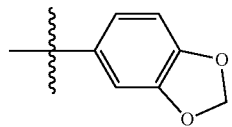 | 423.1 |
| 7 | N-(4-(4-phenyl-5-(trifluoromethyl)oxazol-2-yl)phenyl)benzo[d][1,3]dioxole-5-carboxamide | 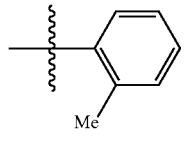 [SMILES: *c1ccccc1C] | 453.1 |
| 8 | 2-methyl-N-(4-(4-phenyl-5-(trifluoromethyl)oxazol-2-yl)phenyl)benzamide | 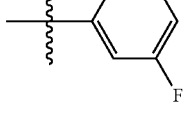 | 349.0 |
| 9 | 3-fluoro-N-(4-(4-phenyl-5-(trifluoromethyl)oxazol-2-yl)phenyl)benzamide | 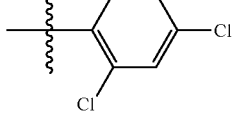 | 427.0 |
| 10 | 2,4-dichloro-N-(4-(4-phenyl-5-(trifluoromethyl)oxazol-2-yl)phenyl)benzamide | 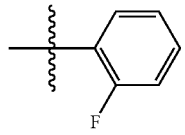 [SMILES: *c1ccccc1F] | 477.0 |
| 11 | 2-fluoro-N-(4-(4-phenyl-5-(trifluoromethyl)oxazol-2-yl)phenyl)benzamide | | 427.1 |

TABLE 1-continued

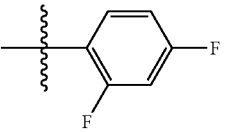 [SMILES: *c1ccc(F)cc1F]

| Example | Compound Name | Ar | MH+ |
|---|---|---|---|
| 12 | 2,4-difluoro-N-(4-(4-phenyl-5-(trifluoromethyl)oxazol-2-yl)phenyl)benzamide | 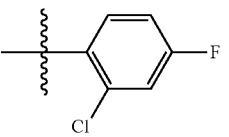 [SMILES: *c1ccc(F)cc1Cl] | 445.0 |
| 13 | 2-chloro-4-fluoro-N-(4-(4-phenyl-5-(trifluoromethyl)oxazol-2-yl)phenyl)benzamide | 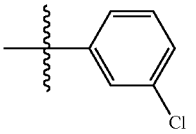 [SMILES: *c1cccc(Cl)c1] | 461.0 |
| 14 | 3-chloro-N-(4-(4-phenyl-5-(trifluoromethyl)oxazol-2-yl)phenyl)benzamide | 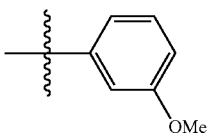 | 443.0 |
| 15 | 3-methoxy-N-(4-(4-phenyl-5-(trifluoromethyl)oxazol-2-yl)phenyl)benzamide | 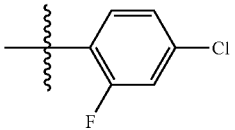 | 439.0 |
| 16 | 4-chloro-2-fluoro-N-(4-(4-phenyl-5-(trifluoromethyl)oxazol-2-yl)phenyl)benzamide | 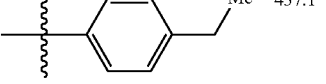 | 461.0 |
| 17 | 4-ethyl-N-(4-(4-phenyl-5-(trifluoromethyl)oxazol-2-yl)phenyl)benzamide | 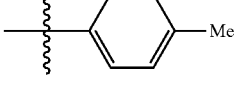 | 437.1 |
| 18 | 4-methyl-N-(4-(4-phenyl-5-(trifluoromethyl)oxazol-2-yl)phenyl)benzamide | 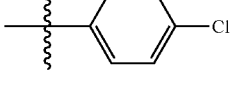 | 423.0 |
| 19 | 4-chloro-N-(4-(4-phenyl-5-(trifluoromethyl)oxazol-2-yl)phenyl)benzamide | 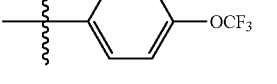 | 443.0 |
| 20 | N-(4-(4-phenyl-5-(trifluoromethyl)oxazol-2-yl)phenyl)-4-(trifluoromethoxy)benzamide | 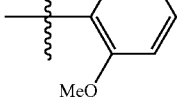 | 493.1 |
| 21 | 2-methoxy-N-(4-(4-phenyl-5-(trifluoromethyl)oxazol-2-yl)phenyl)benzamide | | 439.1 |

TABLE 1-continued

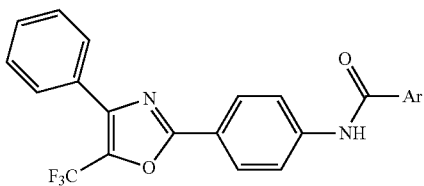

| Example | Compound Name | Ar | MH+ |
|---|---|---|---|
| 22 | N-(4-(4-phenyl-5-(trifluoromethyl)oxazol-2-yl)phenyl)isonicotinamide | 4-pyridyl | 410.0 |
| 23 | 2,6-dichloro-N-(4-(4-phenyl-5-(trifluoromethyl)oxazol-2-yl)phenyl)benzamide | 2,6-dichlorophenyl | 477.0 |
| 24 | N-(4-(4-phenyl-5-(trifluoromethyl)oxazol-2-yl)phenyl)-2-(trifluoromethyl)benzamide | 2-(CF₃)phenyl | 477.1 |
| 25 | 3-cyano-N-(4-(4-phenyl-5-(trifluoromethyl)oxazol-2-yl)phenyl)benzamide | 3-CN-phenyl | 434.0 |
| 26 | N-(4-(4-phenyl-5-(trifluoromethyl)oxazol-2-yl)phenyl)-3-(trifluoromethyl)benzamide | 3-CF₃-phenyl | 477.0 |
| 27 | N-(4-(4-phenyl-5-(trifluoromethyl)oxazol-2-yl)phenyl)cyclohexanecarboxamide | cyclohexyl | 415.0 |
| 28 | 4-cyano-N-(4-(4-phenyl-5-(trifluoromethyl)oxazol-2-yl)phenyl)benzamide | 4-CN-phenyl | 434.0 |
| 29 | 4-(methylsulfonyl)-N-(4-(4-phenyl-5-(trifluoromethyl)oxazol-2-yl)phenyl)benzamide | 4-SO₂Me-phenyl | 487.0 |
| 30 | 2-cyano-N-(4-(4-phenyl-5-(trifluoromethyl)oxazol-2-yl)phenyl)benzamide | 2-CN-phenyl | 434.1 |

Example 31

Compound 31 was synthesized following synthetic method B as shown in Scheme 2.

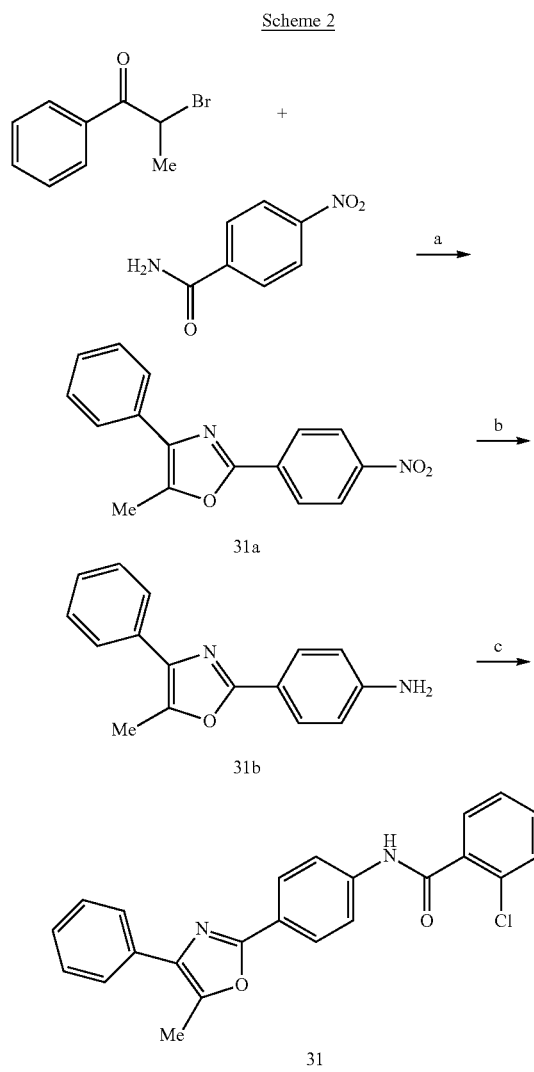

31

(a) N-methylpyrrolidinone, 120° C.; (b) zinc, acetic acid, room temperature; (c) 2,4-dichlorobenzoylchloride, pyridine, dichloromethane, room temperature.

Preparation of 5-methyl-2-(4-nitrophenyl)-4-phenyloxazole (31a): a mixture of 4-nitrobenzamide (6.1 g, 37 mmol) and 2-bromopropiophenone (5.233 g, 25 mmol) in 3 mL NMP was heated to 135° C. After 2 hours at 135° C., the reaction was removed from the oil bath and ca. 30 mL of toluene was added. The resulting mixture was equilibrated to room temperature. After 15 minutes the precipitate was removed by filtration, rinsing with toluene, and discarded. The filtrate was concentrated under reduced pressure and the concentrate taken up in 50 mL ethyl acetate. A precipitate developed and was collected by filtration, rinsing the solid with ethyl acetate and drying under vacuum to afford yellow crystals (1.5 g, 22%). ESI$^+$ m/z=281.0 [MH]$^+$.

Preparation of 4-(5-methyl-4-phenyloxazol-2-yl)benzenamine (31b): to a suspension of 5-methyl-2-(4-nitrophenyl)-4-phenyloxazole (1.20 g, 4.3 mmol) in acetic acid at room temperature was added all at once zinc dust (0.59 ml, 64 mmol). An exotherm developed. The mixture was stirred vigorously for 90 minutes then filtered. The filtrate was concentrated under reduced pressure, diluted with toluene then concentrated under reduced pressure to afford a yellow oily solid (1.1 g, quant.). ESI$^+$ m/z=251.1 [MH]$^+$.

Preparation of 2,4-dichloro-N-(4-(5-methyl-4-phenyloxazol-2-yl)phenyl)benzamide (31): to a solution of 4-(5-methyl-4-phenyloxazol-2-yl)benzenamine (311 mg, 1243 µmol) and pyridine, anhydrous (1013 µl, 12425 µmol) in 4 mL dichloromethane at room temperature was added all at once by metered pipet 2,4-dichlorobenzoyl chloride (192 µl, 1367 µmol). The reaction was stirred at room temperature for 1 hour then concentrated under reduced pressure, triturated with heptane and concentrated under reduced pressure. The residue was triturated with ethyl acetate and the isolated solid (170 mg) was purified by reversed phase preparative HPLC. Fractions containing product were combined and concentrated under reduced pressure. The concentrate was partitioned between dichloromethane and saturated aqueous sodium bicarbonate solution and the organic separation dried over magnesium sulfate, filtered and the filtrate concentrated under reduced pressure to afford a colorless solid (100 mg, 19%). ESI$^+$ m/z=423.0 [MH]$^+$.

Example 32

Compound 32 was synthesized following synthetic method C as shown in Scheme 3.

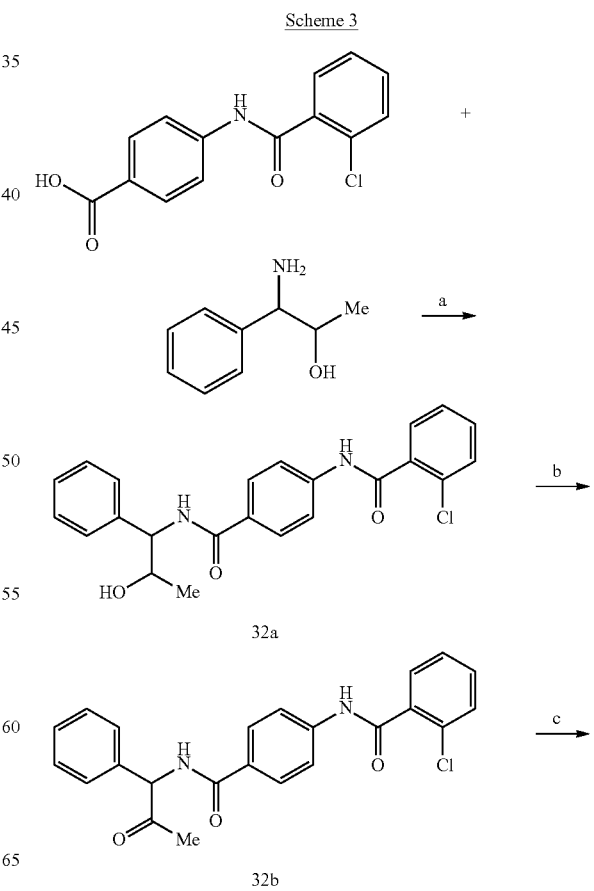

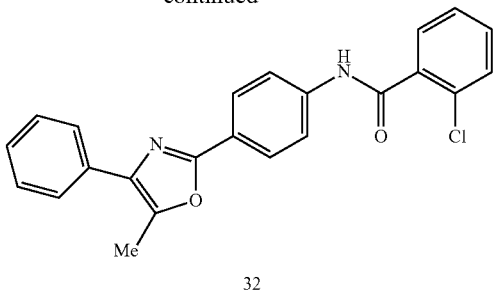

32

(a) NMM, EDC, HOBT, DMF, room temp.; (b) Dess-Martin periodinane, DCM, room temp.; (c) POCl$_3$, pyridine, 70° C.

Preparation of 2-chloro-N-(4-(((2-hydroxy-1-phenylpropyl)amino)carbonyl)phenyl)benzamide (32a): to a room temperature mixture of 1-methylmorpholine (602 mg, 5.95 mmol), 1-hydroxybenzotriazole (322 mg, 2.38 mmol), 1-amino-1-phenylpropan-2-ol (300 mg, 1.98 mmol) and 4-(2-chlorobenzamido)benzoic acid (656 mg, 2.38 mmol) dissolved in 10 mL DMF was added N-(3-dimethylaminopropyl)-N'-ethylcarbodiimide hydrochloride (456 mg, 2.38 mmol) all in one portion. The reaction was left to stir at ambient temperature for 20 hours then poured into 30 mL water. The aqueous mixture was extracted with 50 mL 30% dichloromethane in diethyl ether. The organic extract was washed with 3×25 mL water then 20 mL brine, stirred over magnesium sulfate, filtered and the filtrate concentrated under reduced pressure to afford a white solid. The solid was suspended in hot ethyl acetate, cooled to room temperature and filtered, drying over a stream of air (658 mg, 81%). ESI$^+$ m/z=409.1 [MH]$^+$.

Preparation of 2-chloro-N-(4-(((2-oxo-1-phenylpropyl)amino)carbonyl)phenyl)benzamide (32b): a mixture of 2-chloro-N-(4-(((2-hydroxy-1-phenylpropyl)amino) carbonyl)phenyl)benzamide (294 mg, 719 μmol) and Dess-Martin periodinane (335 mg, 791 μmol) in 5 mL dichloromethane+1 mL DMF was stirred at room temperature for 2 hours then diluted with 20 mL ethyl acetate and washed with 10 mL each water and brine. The organic layer was stirred over magnesium sulfate, filtered and the filtrate concentrated under reduced pressure to afford a yellow solid. The solid was slurried in hot ethyl acetate and left to equilibrate to room temperature. After 48 h, the solid was collected by filtration, rinsing with ethyl acetate and drying over a stream of air (200 mg, 68%). ESI$^+$ m/z=407.0 [MH]$^+$.

Preparation of 2-chloro-N-(4-(5-methyl-4-phenyloxazol-2-yl)phenyl)benzamide (32): a solution of 2-chloro-N-(4-(((2-oxo-1-phenylpropyl)amino)carbonyl)phenyl)benzamide (90 mg, 221 μmol) and phosphoryl trichloride (1.5 mL, 16093 μmol) in 2 mL pyridine was heated in a 70° C. oil bath. After 2 hours the reaction was poured into 10 mL saturated aqueous sodium bicarbonate solution and stirred vigorously for 30 minutes. The aqueous mixture was extracted with 25 mL ethyl acetate. The organic extract was washed with 10 mL each water then brine. The organic layer was stirred over magnesium sulfate, filtered and the filtrate concentrated under reduced pressure to afford a yellow-green oil. TLC indicated a very complex mixture of products. The crude product was purified by reversed-phase preparative HPLC to afford a colorless film (4 mg, 5%). ESI$^+$ m/z=389.0 [MH]$^+$.

Example 33

Compound 33 was synthesized following synthetic Method D as shown in Scheme 4.

Scheme 4

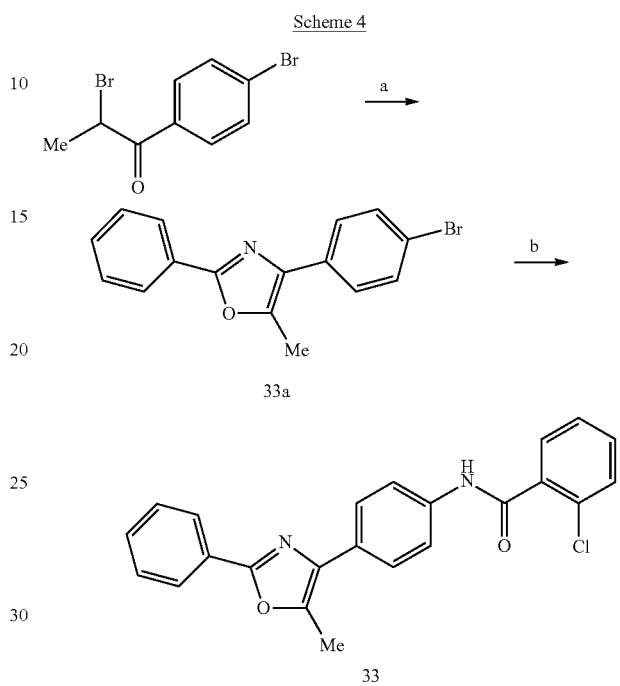

(a) benzamide, 135° C.; (b) 2-chlorobenzamide, cat. CuI, K$_2$CO$_3$, N,N'-dimethylethylenediamine, dioxane, reflux.

Preparation of 4-(4-bromophenyl)-5-methyl-2-phenyloxazole (33a): a mixture of benzamide (4.919 ml, 54.46 mmol) and 2,4'-dibromopropiophenone (10.60 g, 36.31 mmol) was heated in a 135° C. oil bath. The mixture became homogenous at >100° C. The reaction was stirred at 135° C. for 2 hours, after which time a precipitate had developed, and removed from the hot oil bath. Approximately 20 mL of acetonitrile was added to the mixture, which was left to equilibrate to room temperature. The precipitate was collected by filtration, rinsing with acetonitrile to afford a colorless solid. ESI$^+$ m/z=314.0; 316.0 [MH]$^+$.

Preparation of 2-chloro-N-(4-(5-methyl-2-phenyloxazol-4-yl)phenyl)benzamide (33): To a mixture of potassium carbonate (0.898 g, 6.50 mmol), copper(I) iodide (0.0309 g, 0.162 mmol), 2-chlorobenzamide (0.607 g, 3.90 mmol) and 4-(4-bromophenyl)-5-methyl-2-phenyloxazole (1.021 g, 3.25 mmol) in 10 mL 1,4-dioxane was added N,N'-dimethylethylenediamine (0.0350 ml, 0.325 mmol). The reaction was purged with nitrogen twice (evacuated-backfill) then heated in a 110° C. oil bath. After ca. 72 h the reaction was filtered and the filtrate concentrated under reduced pressure. The concentrate was triturated several times with ethyl acetate and the collected solid was discarded. The product was purified from the filtrate by chromatography on silica gel, eluting with 20-60% ethyl acetate in hexane, to afford product as a faintly yellow solid. ESI$^+$ m/z=389.0 [MH]$^+$.

Example 34

Compound 34 was synthesized following synthetic Method E as shown in Scheme 5.

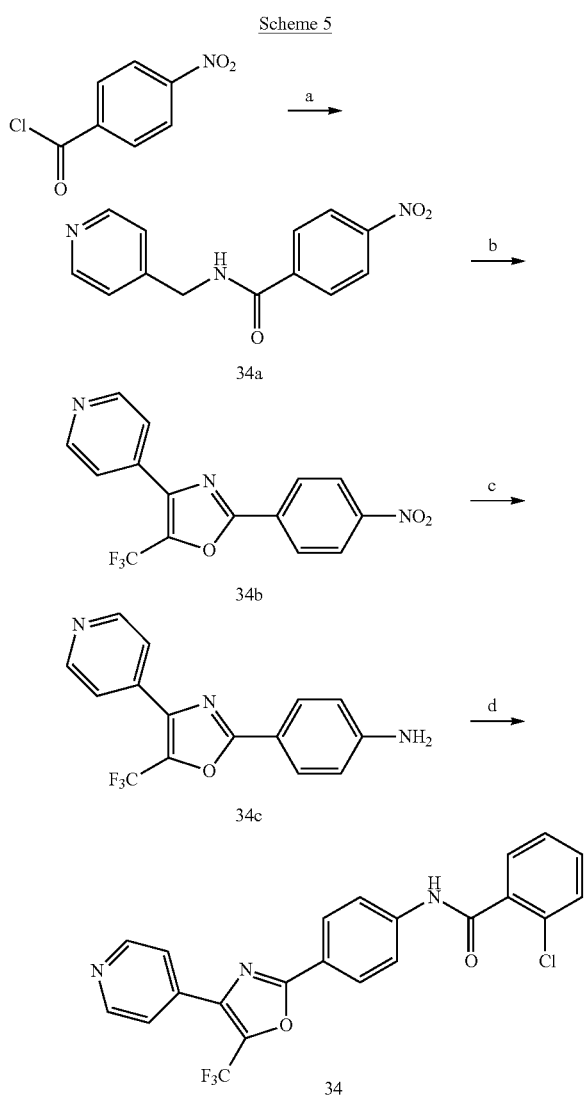

(a) 4-picolylamine, pyridine, DCM, room temp.; (b) trifluoroacetic anhydride, pyridine, toluene, 0° C. -room temp.; (c) hydrogen, Pd on carbon, EtOAc, room temp.; (d) 2-chlorobenzoyl chloride, pyridine, DCM, room temp.

Preparation of 4-nitro-N-(pyridin-4-ylmethyl)benzamide (34a): to a solution of 4-(aminomethyl)pyridine (12.9 ml, 127 mmol) and pyridine (51.4 ml, 636 mmol) in 150 mL dichloromethane cooled by an ice bath was added 4-nitrobenzoyl chloride (24.8 g, 133 mmol) all at once, generating a dark red reaction solution. LC-MS at 5 minutes indicated reaction complete and the desired product predominated. The reaction was stirred at room temperature overnight then the solid collected by filtration. LC-MS indicated that the filtrate was desired product. The solid was washed with 5% aqueous sodium hydroxide solution until aqueous layer was alkaline then the solid collected by filtration. The solid was dried overnight in a vacuum dessicator over $P_2O_5$ (28.4 g, 87%). $ESI^+$ m/z=258.1 $[MH]^+$.

Preparation of 4-(2-(4-nitrophenyl)-5-(trifluoromethyl) oxazol-4-yl)pyridine (34b): to a stirred mixture of 4-nitro-N-(pyridin-4-ylmethyl)benzamide (9.630 g, 37 mmol) and pyridine (36 ml, 449 mmol) in 200 mL toluene cooled by an ice bath was added drop wise by addition funnel trifluoroacetic acid anhydride (32 ml, 225 mmol) over a period of 10 minutes. The reaction was stirred at room temperature overnight then poured into a saturated aqueous sodium bicarbonate solution and stirred vigorously for 1 hour. The organic layer was washed with brine then dried over magnesium sulfate, filtered and the filtrate concentrated under reduced pressure to afford an orange solid. Purified product was isolated by recrystallization from ethyl acetate to afford product as pink needles (7.0 g, 56%). $ESI^+$ m/z=336.0 $[MH]^+$.

Preparation of 4-(4-(pyridin-4-yl)-5-(trifluoromethyl)oxazol-2-yl)benzenamine (34c): to a nitrogen purged flask charged with palladium on carbon (0.032 g, 0.30 mmol) and 4-(2-(4-nitrophenyl)-5-(trifluoromethyl)oxazol-4-yl)pyridine (1.015 g, 3.0 mmol) in 40 mL ethyl acetate was introduced hydrogen (0.0061 g, 3.0 mmol) by balloon. The reaction mixture was stirred at room temperature under an atmosphere of hydrogen for 18 h then purged with nitrogen and filtered through a pad of Celite. The filtrate was concentrated under reduced pressure to afford a yellow solid. The desired product was isolated by chromatography on silica, eluting with 100% ethyl acetate, affording product as a colorless solid (0.52 g, 56%). $ESI^+$ m/z=306.1 $[MH]^+$.

Preparation of 2-chloro-N-(4-(4-(pyridin-4-yl)-5-(trifluoromethyl)oxazol-2-yl)phenyl)benzamide (34): to a stirred mixture of 4-(4-(pyridin-4-yl)-5-(trifluoromethyl)oxazol-2-yl)benzenamine (214 mg, 701 mop and pyridine, anhydrous (0.567 ml, 7011 μmol) in dichloromethane (5.00 ml, 77709 μmol) at room temperature was added 2-chlorobenzoyl chloride (0.0979 ml, 771 μmol) all at once by metered pipet. The reaction was stirred for an hour then concentrated under reduced pressure, taken up in heptane and concentrated under reduced pressure again. The residue was partitioned between dichloromethane and saturated aqueous sodium bicarbonate solution. The organic separation was dried over magnesium sulfate, filtered and filtrate concentrated under reduced pressure to afford a colorless solid. $ESI^+$ m/z=444.1 $[MH]^+$.

Example 35

Compound 35 was synthesized following synthetic Method F as shown in Scheme 6.

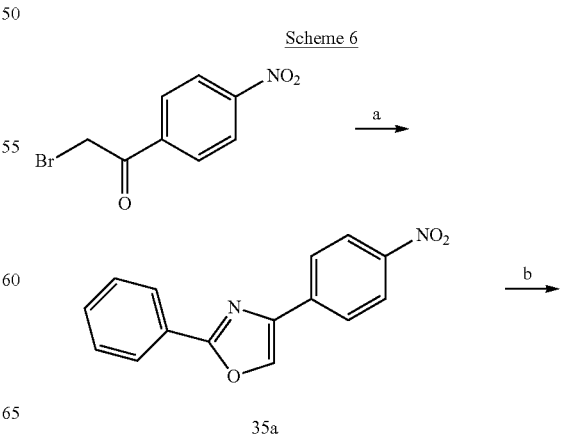

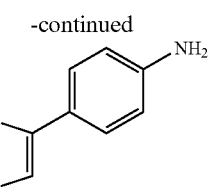

35b

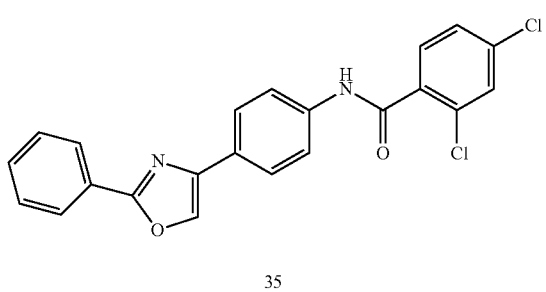

35

(a) benzamide, NMP, 135° C.; (b) Zn, HOAc, room temp.; (c) 2,4-dichlorobenzoyl chloride, pyridine, DCM, room temp.

Preparation of 4-(4-nitrophenyl)-2-phenyloxazole (35a): a mixture of benzamide (3.7 g, 31 mmol), 2-bromo-1-(4-nitrophenyl)ethanone (5.00 g, 20 mmol) and 2.5 mL NMP heated in a 135° C. oil bath. After 30 minutes a precipitate developed. Another 2 mL of NMP was added to dissolve the precipitate. The reaction was heated for a total of 2 hours then removed from the oil bath. The reaction mixture solidified upon cooling. 30-40 mL acetonitrile was added to the solid and the resulting mixture was heated to 90° C. The resulting solution was removed from the oil bath and a precipitate developed upon cooling. The precipitate was collected by filtration (3.4 g, 62%).

Preparation of 4-(2-phenyloxazol-4-yl)benzenamine (35b): zinc dust (0.59 ml, 64 mmol) was added to a mixture of 4-(4-nitrophenyl)-2-phenyloxazole (1.13 g, 4.2 mmol) in acetic acid (20 ml, 349 mmol) at room temperature. An exotherm resulted. The reaction mixture was stirred at room temperature for 60 minutes then filtered, rinsing with ethyl acetate, and the filtrate concentrated under reduced pressure. The concentrate was slurried in toluene and concentrated under reduced pressure to afford a yellow solid (1.0 g, quantitative). ESI⁺ m/z=237.1 [MH]⁺.

Preparation of 2,4-dichloro-N-(4-(2-phenyloxazol-4-yl) phenyl)benzamide (35): to a solution of 4-(2-phenyloxazol-4-yl)benzenamine (299 mg, 1266 µmol) and pyridine (500 µl, 6131 µmol) dissolved in 4 mL dichloromethane at room temperature was added 2,4-dichlorobenzoyl chloride (177 µl, 1266 µmol) all at once. The reaction was stirred at room temperature for 1 hour then concentrated under reduced pressure, taken up in heptane and concentrated again under reduced pressure to afford a yellow solid. The solid was partitioned between dichloromethane and saturated aqueous sodium bicarbonate solution. The organic extract was dried over magnesium sulfate, filtered and the filtrate concentrated under reduced pressure to afford a yellow solid. The product was purified by preparative reversed phase HPLC. Combination of fractions containing product were concentrated under reduced pressure to afford a colorless solid (100 mg, 19%). ESI⁺ m/z=409.0 [MH]⁺.

Example 36

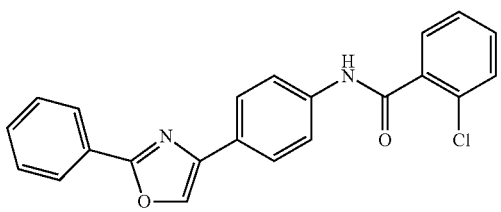

36

Preparation of 2-chloro-N-(4-(2-phenyloxazol-4-yl)phenyl)benzamide (36): compound 36 was prepared from 35b in a similar fashion to compound 35 following Method F, except that 2-chlorobenzoyl chloride was used in place of 2,4-dichlorobenzoyl chloride. ESI⁺ m/z=375.1 [MH]⁺.

Example 37

Compound 37 was synthesized following general synthetic Method B as shown in Scheme 7.

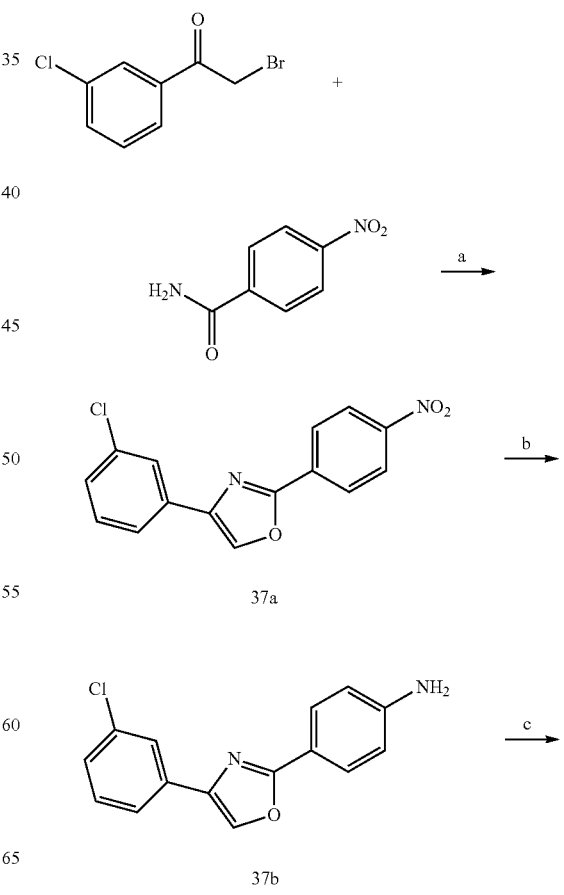

Scheme 7

-continued

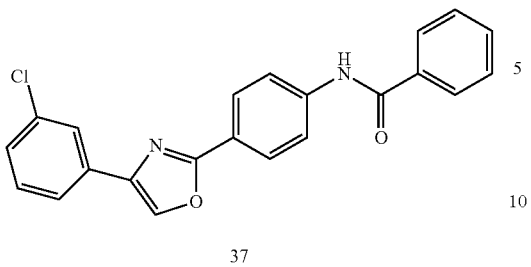

37

(a) NMP, 135° C.; (b) SnCl₂, MeOH; (c) Benzoyl chloride, pyridine, CH₂Cl₂

Preparation of 4-(3-chlorophenyl)-2-(4-nitrophenyl)oxazole (37a): under an $N_2$ atmosphere, 4-nitrobenzamide (5.3 g, 32 mmol) and 3-chlorophenacyl bromide (4.9 g, 21 mmol) were combined in NMP (3.0 mL) and heated to 135° C. After 2.5 hours at 135° C., the reaction was diluted with 20 mL of toluene and allowed to cool to room temperature. The solid was removed by filtration and the filtrate was concentrated in vacuo. The resulting solid from concentration of the filtrate was triturated with ethyl acetate. The solid was collected by filtration and afforded 4-(3-chlorophenyl)-2-(4-nitrophenyl)oxazole (2.74 g, 43% yield). ESI m/z=301.0 (M+H⁺).

Preparation of 4-(4-(3-chlorophenyl)oxazol-2-yl)benzenamine (37b): under an $N_2$ atmosphere, was 4-(3-chlorophenyl)-2-(4-nitrophenyl)oxazole (2.65 g, 8.81 mmol) suspended in methanol (20.0 mL) and tin(II) chloride dihydrate (7.95 g, 35.3 mmol) was added. The reaction was stirred at room temperature for ca. 72 h. LC-MS showed the reaction was not complete. The reaction was heated to 60° C. for 5 hours. The reaction was then diluted with ethyl acetate and washed with 0.1N HCl, followed by 5% NaHCO₃ and brine. The organic layer was then dried (Na₂SO₄), filtered and concentrated in vacuo. The crude residue was purified by chromatography on silica gel, eluting with 20% to 40% ethyl acetate in hexanes. The resulting solid was triturated with ethyl acetate/hexanes and the resulting solid was collected by filtration to afford 4-(4-(3-chlorophenyl)oxazol-2-yl)benzenamine (0.898 g, 37.6% yield). ESI m/z=271.0 (M+H⁺).

Preparation of N-(4-(4-(3-chlorophenyl)oxazol-2-yl)phenyl)benzamide (37): under an $N_2$ atmosphere, 4-(4-(3-chlorophenyl)oxazol-2-yl)benzenamine (0.127 g, 0.469 mmol) was dissolved in dichloromethane (4.00 ml, 62.2 mmol). Benzoyl chloride (0.0572 ml, 0.493 mmol) was added followed by pyridine (0.200 ml, 2.47 mmol), and the reaction was allowed to stir at room temperature for 2.5 hours. The reaction was diluted with ethyl acetate and washed with 0.1N N HCl, and 5% NaHCO₃. The organic layer was dried (Na₂SO₄), filtered and concentrated in vacuo. The crude solid was triturated with ethyl acetate/hexanes and the resulting solid was collected by filtration to afford N-(4-(4-(3-chlorophenyl)oxazol-2-yl)phenyl)benzamide (0.112 g, 63.7% yield). ESI m/z=375.1 (M+H⁺).

Example 38

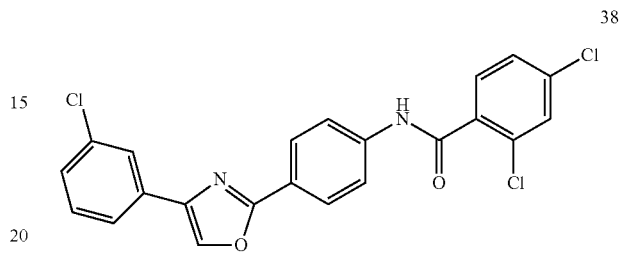

38

Compound 38, 2,4-dichloro-N-(4-(4-(3-chlorophenyl)oxazol-2-yl)phenyl)benzamide, was prepared analogously to example 37 according to synthetic method B except that 2,4-dichlorobenzoyl chloride was used instead of benzoyl chloride in step c. ESI m/z=443.0 (M+H⁺).

Example 39

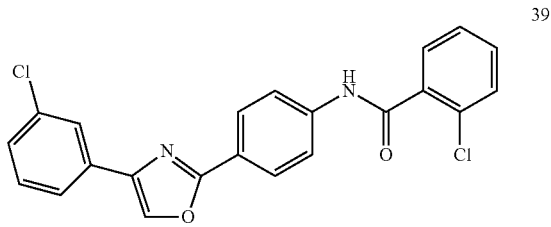 [SMILES: O=C(Nc1ccc(-c2nc(-c3cccc(Cl)c3)co2)cc1)c1ccccc1Cl]

39

Compound 39, 2-chloro-N-(4-(4-(3-chlorophenyl)oxazol-2-yl)phenyl)benzamide, was prepared analogously to example 37 according to synthetic method B except that 2-chlorobenzoyl chloride was used instead of benzoyl chloride in step c. ESI m/z=409.0 (M+H⁺).

Examples 40-45

Compounds 40-45 were prepared analogously to Example 37 according to synthetic method B except that 2-chlorophenacyl bromide was used instead of 3-chlorophenacyl bromide in step a and the appropriate substituted benzoyl chloride was used in step c to afford the corresponding product shown in the table below.

TABLE 2

| Example | Name | Ar | MH+ |
|---|---|---|---|
| 40 | 2-chloro-N-(4-(4-(2-chlorophenyl)oxazol-2-yl)phenyl)benzamide | 2-chlorophenyl | 409.0 |
| 41 | N-(4-(4-(2-chlorophenyl)oxazol-2-yl)phenyl)-4-methoxy-2-methylbenzamide | 4-methoxy-2-methylphenyl | 419.0 |
| 42 | 2,6-dichloro-N-(4-(4-(2-chlorophenyl)oxazol-2-yl)phenyl)benzamide | 2,6-dichlorophenyl | 442.9 |
| 43 | 2,4-dichloro-N-(4-(4-(2-chlorophenyl)oxazol-2-yl)phenyl)benzamide | 2,4-dichlorophenyl | 443.0 |
| 44 | N-(4-(4-(2-chlorophenyl)oxazol-2-yl)phenyl)-2-methylbenzamide | 2-methylphenyl | 389.0 |
| 45 | N-(4-(4-(2-chlorophenyl)oxazol-2-yl)phenyl)benzamide | phenyl | 375.1 |

Examples 46-48

Compounds 46-48 were prepared analogously to example 37 according to synthetic method B except that 4-fluorophenacyl bromide was used instead of 3-chlorophenacyl bromide in step a and the appropriate substituted benzoyl chloride was used in step c to afford the corresponding product shown in the table below.

TABLE 3

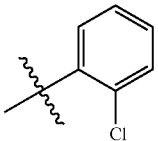 [SMILES: *c1ccccc1Cl]

| Example | Name | Ar | MH+ |
|---|---|---|---|
| 46 | 2-chloro-N-(4-(4-(4-fluorophenyl)oxazol-2-yl)phenyl)benzamide | 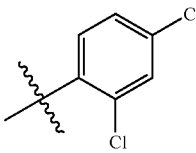 | 393.1 |
| 47 | 2,4-dichloro-N-(4-(4-(4-fluorophenyl)oxazol-2-yl)phenyl)benzamide | 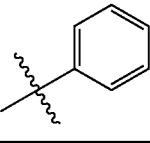 | 427.0 |
| 48 | N-(4-(4-(4-fluorophenyl)oxazol-2-yl)phenyl)benzamide | 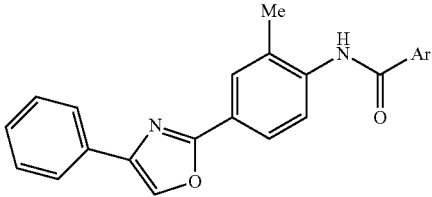 | 359.0 |

Examples 49-51

Compounds 49-51 were prepared analogously to example 37 according to synthetic method B except that phenacyl bromide was used instead of 3-chlorophenacyl bromide and 4-nitro-3-methylbenzamide was used instead of 4-nitrobenzamide in step a and the appropriate substituted benzoyl chloride was used in step c to afford the corresponding product shown in the table below.

TABLE 4

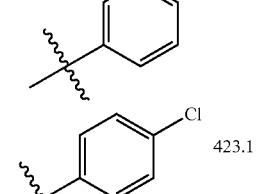

| Example | Name | Ar | MH+ |
|---|---|---|---|
| 49 | N-(2-methyl-4-(4-phenyloxazol-2-yl)phenyl)benzamide | 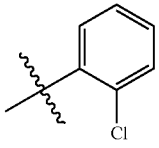 [SMILES: *c1ccccc1Cl] | 355.1 |
| 50 | 2,4-dichloro-N-(2-methyl-4-(4-phenyloxazol-2-yl)phenyl)benzamide | | 423.1 |
| 51 | 2-chloro-N-(2-methyl-4-(4-phenyloxazol-2-yl)phenyl)benzamide | | 389.0 |

Examples 52-54

Compounds 52-54 were prepared analogously to example 37 according to synthetic method B except that phenacyl bromide was used instead of 3-chlorophenacyl bromide and 4-nitro-2-chlorobenzamide was used instead of 4-nitrobenzamide in step a and the appropriate substituted benzoyl chloride was used in step c to afford the corresponding product shown in the table below.

TABLE 5

| Example | Name | Ar | MH+ |
|---|---|---|---|
| 52 | N-(3-chloro-4-(4-phenyloxazol-2-yl)phenyl)benzamide | phenyl | 375.1 |
| 53 | 2-chloro-N-(3-chloro-4-(4-phenyloxazol-2-yl)phenyl)benzamide | 2-chlorophenyl | 409.0 |
| 54 | 2,4-dichloro-N-(3-chloro-4-(4-phenyloxazol-2-yl)phenyl)benzamide | 2,4-dichlorophenyl | 443.0 |

Example 55

Compound 55 was synthesized following synthetic method E as shown in Scheme 8.

Scheme 8

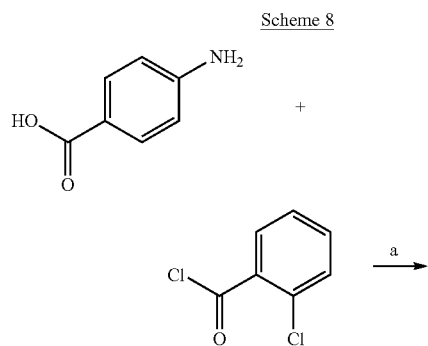

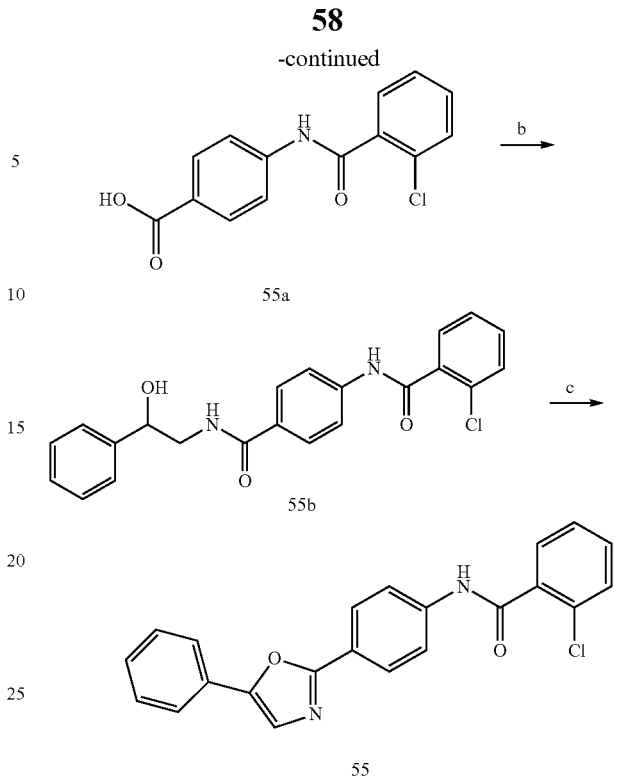

(a) NEt₃, MeCN, room temp.; (b) 2-amino-1-phenylethanol, EDC, HOBT, NEt₃, DMF, room temp.; (c) i. Dess-Martin periodinane, DMF, room temp.; ii. POCl₃, pyridine, 70° C.

Preparation of 4-(2-chlorobenzamido)benzoic acid (55a): under an N₂ atmosphere, 4-aminobenzoic acid (2.50 g, 18.2 mmol) was dissolved in acetonitrile (100 ml) and treated with 2-chlorobenzoyl chloride (2.43 ml, 19.1 mmol). Triethylamine (2.66 ml, 19.1 mmol) was added and the reaction was allowed to stir at room temperature for four hours. The reaction was concentrated in vacuo, and the resulting solid was partitioned between Et₂O and 0.5N NaOH. The layers were separated and the organic layer was discarded. The aqueous layer was acidified to pH 2 with HCl and the aqueous layer was extracted with ethyl acetate. The organic layer was dried Na₂SO₄, filtered and concentrated in vacuo. The resulting solid was triturated with Et₂O, and the solid was collected by filtration to afford 4-(2-chlorobenzamido)benzoic acid (2.72 g, 54.2% yield). ESI m/z=276.1 (M+H⁺).

Preparation of 2-chloro-N-(4-(((2-hydroxy-2-phenylethyl)amino)carbonyl)phenyl)-benzamide (55b): under an N₂ atmosphere, 4-(2-chlorobenzamido)benzoic acid (0.500 g, 1.81 mmol) was dissolved in N,N-dimethylformamide (10.0 ml) and the solution was treated with N-3-dimethylaminopropyl)-N'-ethylcarbodiimide hydrochloride (0.696 g, 3.62 mmol), 1-hydroxybenzotriazole hydrate (0.491 g, 3.62 mmol), 2-amino-1-phenylethanol (0.498 g, 3.62 mmol), and triethylamine (0.506 ml, 3.62 mmol). The reaction was allowed to stir at room temperature overnight. The reaction was diluted with ethyl acetate and washed with 0.5N HCl followed by 5% NaHCO₃. The organic layer was dried (Na₂SO₄), and concentrated in vacuo. The resulting solid was triturated with a mixture of ethyl acetate and hexanes to afford 2-chloro-N-(4-(((2-hydroxy-2-phenylethyl)amino)carbonyl)phenyl)benzamide (0.578 g, 71.5%) after collecting the solid by filtration. ESI m/z=395.0 (M+H⁺).

Preparation of 2-chloro-N-(4-(5-phenyloxazol-2-yl)phenyl)benzamide (55): under an N₂ atmosphere, 2-chloro-N-(4-

(((2-hydroxy-2-phenylethyl)amino)carbonyl)phenyl)benzamide (0.578 g, 1.46 mmol) was dissolved in DMF (7.00 ml). Dess-Martin periodinane (0.745 g, 1.76 mmol) was added and the reaction was stirred at room temperature for 3 hours. The reaction was diluted with ethyl acetate and a saturated aqueous solution of sodium bisulfate. The layers were separated and the organic layer was washed with water and brine. The organic layer was dried ($Na_2SO_4$), filtered and concentrated in vacuo. The residue was triturated with ethyl acetate and hexanes. The resulting solid was collected by filtration. The solid was suspended in pyridine (8.00 ml) and $POCl_3$ (4.00 ml). The reaction was heated to 70° C. for 3 hours. The reaction was poured into a cooled 5% $NaHCO_3$ solution and stirred vigorously for 15 minutes. The mixture was then extracted with ethyl acetate. The organic layer was dried ($Na_2SO_4$), filtered and concentrated in vacuo. The crude residue was purified by column chromatography eluting with 25% to 50% ethyl acetate in hexanes. The resulting solid was triturated with ethyl acetate/hexanes and collected by filtration to afford 2-chloro-N-(4-(5-phenyloxazol-2-yl)phenyl) benzamide (0.920 g, 16.8%). ESI m/z=375.0 (M+H$^+$).

Example 56

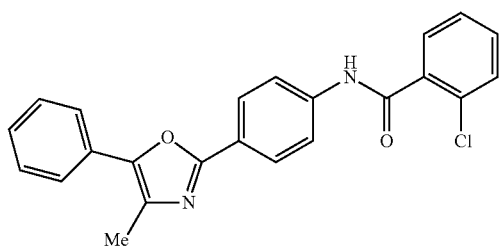

56

Compound 56, 2-chloro-N-(4-(4-methyl-5-phenyloxazol-2-yl)phenyl)benzamide, was made analogously to example 55 according to synthetic Method G, except that (1S,2R)-(+)-norephedrine was used instead of 2-amino-1-phenylethanol in step b. ESI m/z=389.0 (M+H$^+$).

Example 57

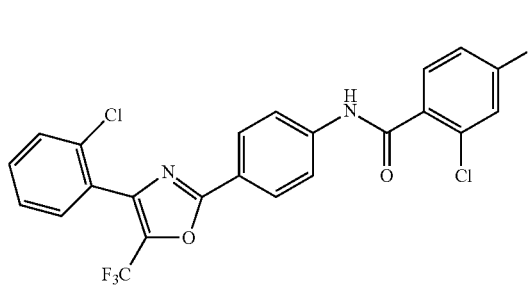

57

Compound 57, 2,4-dichloro-N-(4-(4-(2-chlorophenyl)-5-(trifluoromethyl)oxazol-2-yl)phenyl)benzamide, was made analogously to Example 1 according to synthetic method A except that methyl 2-amino-2-(2-chlorophenyl)acetate was used instead of methyl 2-amino-2-phenylacetate in step a and 2,4-dichlorobenzoyl chloride was used instead of 2-chlorobenzoyl chloride in step f. ESI$^+$ m/z=512.0 [MH]$^+$.

Example 58

Smoothened Receptor Activity

Antagonist activity of compounds for mouse Smoothened was assessed by measuring inhibition of Luciferase activity in Shh-stimulated NIH-3T3 cells stably transfected with a luciferase reporter construct with 5 GLI binding sites upstream of a basal promoter, similar to methods described by others. Chen et al. (2002) *PNAS* 99 14071-14076; Taipale et al. (2000) *Nature* 406 1005-1009. Antagonist activity of compounds on human Smoothened was assessed by measuring inhibition of GLI1 transcription in Shh-stimulated HEPM cells (American Type Culture Collection, Manassas, Va. USA), similar to methods described by others. See U.S. Pat. No. 6,613,798. For this work GLI1 transcription in HEPM cells was measured using a Quantigene assay specific for GLI1 (Panomics Inc., Freemont, Calif., USA) in place of PCR based methods.

All exemplified compounds demonstrated antagonism of human Smoothened with IC$_{50}$'s of 1 μM or less.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of Formula I

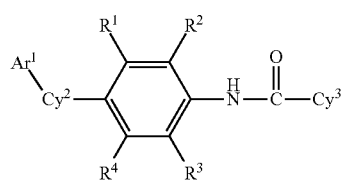

I or a pharmaceutically acceptable salt thereof, wherein

Ar$^1$ is phenyl or pyridinyl optionally substituted independently with 1-5 substituents, wherein the substituents are selected from the group consisting of $C_{1-8}$alkyl, $C_{2-8}$alkenyl, $C_{2-8}$alkynyl, $C_{1-6}$haloalkyl, halogen, cyano, hydroxy, oxo, —NR$^a$R$^b$ and —OR$^c$;

R$^1$, R$^2$, R$^3$, and R$^4$ are each independently selected from H, $C_{1-6}$alkyl, $C_{3-6}$cycloalkyl, $C_{1-6}$haloalkyl, halogen, oxo, —C(=O)OR$^a$, —R$^c$OH, —OR$^c$, —NR$^a$R$^b$, NR$^a$C(=O)R$^b$, —C(=O)OR$^c$, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and S(=O)$_m$R$^c$;

R$^a$, R$^b$, and R$^c$ are each independently selected from H, $C_{1-8}$alkyl, $C_{2-8}$alkenyl, $C_{2-8}$alkynyl, $C_{1-6}$haloalkyl, heterocyclyl, aryl, and heteroaryl;

Cy² is selected from the group consisting of

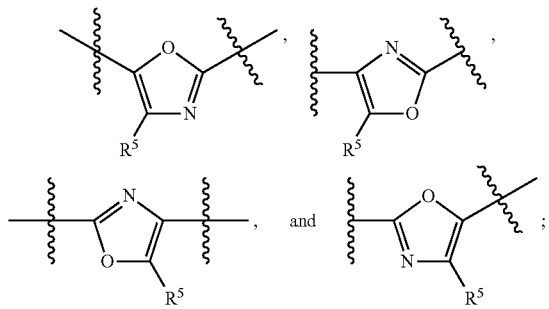

R⁵ is H, $C_{1-6}$alkyl, $C_{3-6}$cycloalkyl, or $C_{1-6}$haloalkyl;
Cy³ is a partially or fully saturated or unsaturated 6-membered monocyclic ring formed of carbon atoms optionally including 1-3 heteroatoms selected from the group consisting of O, N, and S, wherein the ring is optionally substituted independently with 1-5 substituents, wherein the substituents are independently selected from the group consisting of $C_{1-8}$alkyl, $C_{2-8}$alkenyl, $C_{2-8}$alkynyl, $C_{1-6}$haloalkyl, halogen, cyano, hydroxy, oxo, —C(=O)OR$^c$, —R$^c$OH, —OR$^c$, —NR$^a$R$^b$, NR$^a$C(=O)R$^b$, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and S(=O)$_m$R$^c$, wherein the substituents can be fused forming a 5- or 6-membered saturated or unsaturated cycle optionally containing 1-3 heteroatoms selected from the group consisting of O, N, and S;
provided that at least one of Ar¹ or Cy³ is substituted with at least one substituent or R⁵ is not H.

2. The compound of claim 1, or a pharmaceutically acceptable salt thereof, wherein Ar¹ is optionally substituted independently with 1-5 substituents, wherein the substituents are selected from the group consisting of $C_{1-8}$alkyl, $C_{2-8}$alkenyl, $C_{2-8}$alkynyl, $C_{1-6}$haloalkyl, halogen, cyano, hydroxy, oxo, —NR$^a$R$^b$ and —OR$^c$.

3. The compound of claim 1, or a pharmaceutically acceptable salt thereof, wherein Ar¹ is unsubstituted pyridinyl.

4. The compound of claim 1, or a pharmaceutically acceptable salt thereof, wherein Ar¹ is phenyl optionally substituted independently with 1-5 substituents, wherein the substituents are selected from the group consisting of $C_{1-8}$alkyl, $C_{2-8}$alkenyl, $C_{2-8}$alkynyl, $C_{1-6}$haloalkyl, halogen, cyano, hydroxy, oxo, —NR$^a$R$^b$ and —OR$^c$.

5. The compound of claim 4, or a pharmaceutically acceptable salt thereof, wherein phenyl is substituted with 1 substituent selected from the group consisting of $C_{1-6}$haloalkyl and halogen.

6. The compound of claim 5, or a pharmaceutically acceptable salt thereof, wherein halogen is chlorine.

7. The compound of claim 1 represented by Formula II

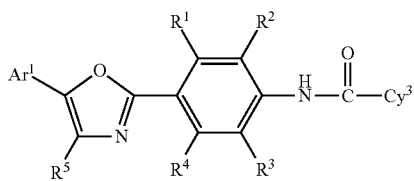

or a pharmaceutically acceptable salt thereof.

8. The compound of claim 1 represented by Formula III

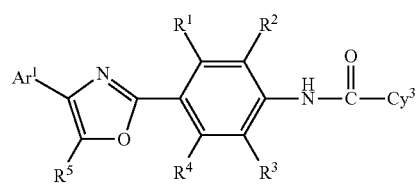

or a pharmaceutically acceptable salt thereof.

9. The compound of claim 1 represented by Formula IV

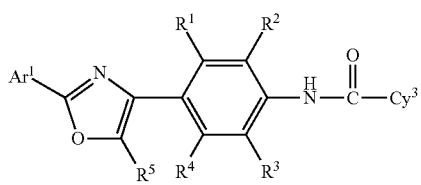

or a pharmaceutically acceptable salt thereof.

10. The compound of claim 1 represented by Formula V

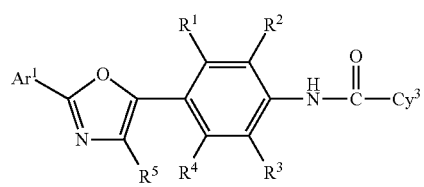

or a pharmaceutically acceptable salt thereof.

11. The compound of claim 1 or a pharmaceutically acceptable salt thereof, wherein R⁵ is $C_{1-6}$alkyl or $C_{1-6}$haloalkyl.

12. The compound of claim 1 or a pharmaceutically acceptable salt thereof, wherein R⁵ is methyl or ethyl.

13. The compound of claim 10 or a pharmaceutically acceptable salt thereof, wherein R⁵ is trifluoromethyl.

14. The compound of claim 1 or a pharmaceutically acceptable salt thereof, wherein R¹, R², R³, and R⁴ are each independently selected from H, $C_{1-6}$alkyl, $C_{3-6}$cycloalkyl, and $C_{1-6}$haloalkyl.

15. The compound of claim 1 or a pharmaceutically acceptable salt thereof, wherein R¹, R², R³, and R⁴ are each independently H.

16. The compound of claim 1 or a pharmaceutically acceptable salt thereof, wherein Cy³ is optionally substituted phenyl.

17. The compound of claim 16 or a pharmaceutically acceptable salt thereof, wherein the substituents are independently selected from the group consisting of $C_{1-8}$alkyl, $C_{2-8}$alkenyl, $C_{2-8}$alkynyl, $C_{1-6}$haloalkyl, halogen, cyano and —OR$^c$.

18. The compound of claim 1 or a pharmaceutically acceptable salt thereof, wherein Cy³ is optionally substituted cyclohexyl.

19. The compound of claim 1, wherein the compound is selected from the group consisting of:
2-chloro-N-(4-(4-phenyl-5-(trifluoromethyl)oxazol-2-yl)phenyl)benzamide, 2-fluoro-4-methoxy-N-(4-(4-phenyl-5-(trifluoromethyl)oxazol-2-yl)phenyl)benzamide,
4-methoxy-N-(4-(4-phenyl-5-(trifluoromethyl)oxazol-2-yl)phenyl)benzamide,
4-fluoro-N-(4-(4-phenyl-5-(trifluoromethyl)oxazol-2-yl)phenyl)benzamide,
N-(4-(4-phenyl-5-(trifluoromethyl)oxazol-2-yl)phenyl)benzamide,
3-methyl-N-(4-(4-phenyl-5-(trifluoromethyl)oxazol-2-yl)phenyl)benzamide,
N-(4-(4-phenyl-5-(trifluoromethyl)oxazol-2-yl)phenyl)benzo[d][1,3]dioxole-5-carboxamide,
2-methyl-N-(4-(4-phenyl-5-(trifluoromethyl)oxazol-2-yl)phenyl)benzamide,
3-fluoro-N-(4-(4-phenyl-5-(trifluoromethyl)oxazol-2-yl)phenyl)benzamide,
2,4-dichloro-N-(4-(4-phenyl-5-(trifluoromethyl)oxazol-2-yl)phenyl)benzamide,
2-fluoro-N-(4-(4-phenyl-5-(trifluoromethyl)oxazol-2-yl)phenyl)benzamide,
2,4-difluoro-N-(4-(4-phenyl-5-(trifluoromethyl)oxazol-2-yl)phenyl)benzamide,
2-chloro-4-fluoro-N-(4-(4-phenyl-5-(trifluoromethyl)oxazol-2-yl)phenyl)benzamide,
3-chloro-N-(4-(4-phenyl-5-(trifluoromethyl)oxazol-2-yl)phenyl)benzamide,
3-methoxy-N-(4-(4-phenyl-5-(trifluoromethyl)oxazol-2-yl)phenyl)benzamide,
4-chloro-2-fluoro-N-(4-(4-phenyl-5-(trifluoromethyl)oxazol-2-yl)phenyl)benzamide,
4-ethyl-N-(4-(4-phenyl-5-(trifluoromethyl)oxazol-2-yl)phenyl)benzamide,
4-methyl-N-(4-(4-phenyl-5-(trifluoromethyl)oxazol-2-yl)phenyl)benzamide,
4-chloro-N-(4-(4-phenyl-5-(trifluoromethyl)oxazol-2-yl)phenyl)benzamide,
N-(4-(4-phenyl-5-(trifluoromethyl)oxazol-2-yl)phenyl)-4-(trifluoromethoxy)benzamide,
2-methoxy-N-(4-(4-phenyl-5-(trifluoromethyl)oxazol-2-yl)phenyl)benzamide,
N-(4-(4-phenyl-5-(trifluoromethyl)oxazol-2-yl)phenyl)isonicotinamide,
2,6-dichloro-N-(4-(4-phenyl-5-(trifluoromethyl)oxazol-2-yl)phenyl)benzamide,
N-(4-(4-phenyl-5-(trifluoromethyl)oxazol-2-yl)phenyl)-2-(trifluoromethyl)benzamide,
3-cyano-N-(4-(4-phenyl-5-(trifluoromethyl)oxazol-2-yl)phenyl)benzamide,
N-(4-(4-phenyl-5-(trifluoromethyl)oxazol-2-yl)phenyl)-3-(trifluoromethyl)benzamide,
N-(4-(4-phenyl-5-(trifluoromethyl)oxazol-2-yl)phenyl)cyclohexanecarboxamide,
4-cyano-N-(4-(4-phenyl-5-(trifluoromethyl)oxazol-2-yl)phenyl)benzamide,
4-(methylsulfonyl)-N-(4-(4-phenyl-5-(trifluoromethyl)oxazol-2-yl)phenyl)benzamide,
2-cyano-N-(4-(4-phenyl-5-(trifluoromethyl)oxazol-2-yl)phenyl)benzamide,
2,4-dichloro-N-(4-(5-methyl-4-phenyloxazol-2-yl)phenyl)benzamide,
2-chloro-N-(4-(5-methyl-4-phenyloxazol-2-yl)phenyl)benzamide,
2-chloro-N-(4-(5-methyl-2-phenyloxazol-4-yl)phenyl)benzamide,
2-chloro-N-(4-(4-(pyridin-4-yl)-5-(trifluoromethyl)oxazol-2-yl)phenyl)benzamide,
2,4-dichloro-N-(4-(2-phenyloxazol-4-yl)phenyl)benzamide,
2-chloro-N-(4-(2-phenyloxazol-4-yl)phenyl)benzamide,
N-(4-(4-(3-chlorophenyl)oxazol-2-yl)phenyl)benzamide,
2,4-dichloro-N-(4-(4-(3-chlorophenyl)oxazol-2-yl)phenyl)benzamide
2-chloro-N-(4-(4-(3-chlorophenyl)oxazol-2-yl)phenyl)benzamide
2-chloro-N-(4-(4-(2-chlorophenyl)oxazol-2-yl)phenyl)benzamide,
N-(4-(4-(2-chlorophenyl)oxazol-2-yl)phenyl)-4-methoxy-2-methylbenzamide,
2,6-dichloro-N-(4-(4-(2-chlorophenyl)oxazol-2-yl)phenyl)benzamide,
2,4-dichloro-N-(4-(4-(2-chlorophenyl)oxazol-2-yl)phenyl)benzamide,
N-(4-(4-(2-chlorophenyl)oxazol-2-yl)phenyl)-2-methylbenzamide,
N-(4-(4-(2-chlorophenyl)oxazol-2-yl)phenyl)benzamide,
2-chloro-N-(4-(4-(4-fluorophenyl)oxazol-2-yl)phenyl)benzamide,
2,4-dichloro-N-(4-(4-(4-fluorophenyl)oxazol-2-yl)phenyl)benzamide,
N-(4-(4-(4-fluorophenyl)oxazol-2-yl)phenyl)benzamide,
N-(2-methyl-4-(4-phenyloxazol-2-yl)phenyl)benzamide,
2,4-dichloro-N-(2-methyl-4-(4-phenyloxazol-2-yl)phenyl)benzamide,
2-chloro-N-(2-methyl-4-(4-phenyloxazol-2-yl)phenyl)benzamide,
N-(3-chloro-4-(4-phenyloxazol-2-yl)phenyl)benzamide,
2-chloro-N-(3-chloro-4-(4-phenyloxazol-2-yl)phenyl)benzamide,
2,4-dichloro-N-(3-chloro-4-(4-phenyloxazol-2-yl)phenyl)benzamide,
2-chloro-N-(4-(5-phenyloxazol-2-yl)phenyl)benzamide,
2-chloro-N-(4-(4-methyl-5-phenyloxazol-2-yl)phenyl)benzamide, and
2,4-dichloro-N-(4-(4-(2-chlorophenyl)-5-(trifluoromethyl)oxazol-2-yl)phenyl)benzamide,
or a pharmaceutically acceptable salt thereof.

20. A pharmaceutical composition comprising a compound of claim 1 or a pharmaceutically acceptable salt thereof and a pharmaceutically acceptable carrier.

21. A pharmaceutical composition comprising a compound of claim 19 or a pharmaceutically acceptable salt thereof and a pharmaceutically acceptable carrier.

* * * * *